US011266985B2

(12) United States Patent
Horii et al.

(10) Patent No.: US 11,266,985 B2
(45) Date of Patent: Mar. 8, 2022

(54) LIQUID SEALED CARTRIDGE, METHOD FOR PRODUCING LIQUID SEALED CARTRIDGE, AND LIQUID SENDING METHOD

(71) Applicant: SYSMEX CORPORATION, Kobe (JP)

(72) Inventors: Kazuyoshi Horii, Kobe (JP); Takao Fujiwara, Kobe (JP); Tomoyuki Nose, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 522 days.

(21) Appl. No.: 15/801,580

(22) Filed: Nov. 2, 2017

(65) Prior Publication Data

US 2018/0126377 A1 May 10, 2018

(30) Foreign Application Priority Data

Nov. 4, 2016 (JP) .............................. JP2016-216665

(51) Int. Cl.
*G01N 35/10* (2006.01)
*G01N 1/14* (2006.01)
(Continued)

(52) U.S. Cl.
CPC ..... *B01L 3/502707* (2013.01); *B01L 3/50273* (2013.01); *B01L 3/502738* (2013.01); *G01N 33/491* (2013.01); *G01N 35/00069* (2013.01); *G01N 35/0098* (2013.01); *B01L 2200/0605* (2013.01); *B01L 2200/0621* (2013.01); *B01L 2200/16* (2013.01); *B01L 2300/0803* (2013.01);
(Continued)

(58) Field of Classification Search
CPC combination set(s) only.
See application file for complete search history.

(56) References Cited

U.S. PATENT DOCUMENTS 6,591,852 B1    7/2003  McNeely et al.
2009/0155927 A1  6/2009  Higashino et al.
(Continued)

FOREIGN PATENT DOCUMENTS

CN    101121336 A    2/2008
CN    103660587 A    3/2014
(Continued)

OTHER PUBLICATIONS

Communication pursuant to Article 94(3) EPC issued on Jun. 26, 2019 in a counterpart European patent application No. 17199662.2.
(Continued)

*Primary Examiner* — Brian R Gordon
(74) *Attorney, Agent, or Firm* — Crowell & Moring LLP

(57) ABSTRACT

Disclosed is a liquid sealed cartridge in which a liquid injected through an inlet is previously sealed, and the liquid is transferred by a centrifugal force being applied by rotation, and the liquid sealed cartridge includes: a liquid storage portion configured to store the liquid; a bypass flow path having one end and the other end connected to the liquid storage portion, the bypass flow path having the inlet; and a transfer flow path into which the liquid is transferred from the liquid storage portion when the centrifugal force is applied.

14 Claims, 16 Drawing Sheets

(51) Int. Cl.
- G01N 1/18 (2006.01)
- B01L 3/00 (2006.01)
- B01L 3/02 (2006.01)
- G01N 35/00 (2006.01)
- G01N 33/49 (2006.01)
- G01N 21/76 (2006.01)
- B65B 3/12 (2006.01)

(52) U.S. Cl.
CPC ............... *B01L 2300/0887* (2013.01); *B01L 2400/0409* (2013.01); *B01L 2400/0475* (2013.01); *B01L 2400/0683* (2013.01); *B01L 2400/0688* (2013.01); *B65B 3/12* (2013.01); *G01N 21/76* (2013.01); *G01N 2035/00089* (2013.01); *G01N 2035/00495* (2013.01)

(56) References Cited

U.S. PATENT DOCUMENTS

| | | |
|---|---|---|
| 2010/0015715 A1 | 1/2010 | Cho et al. |
| 2010/0120166 A1 | 5/2010 | Ozaki et al. |
| 2010/0279392 A1 | 11/2010 | Kodama et al. |
| 2011/0020194 A1* | 1/2011 | Lee .................. B01L 3/50273 422/400 |
| 2011/0104009 A1 | 5/2011 | Kawamura et al. |
| 2013/0337578 A1 | 12/2013 | Delamarche et al. |
| 2014/0061961 A1 | 3/2014 | Ishizawa et al. |

FOREIGN PATENT DOCUMENTS

| | | |
|---|---|---|
| EP | 1525916 | 4/2005 |
| EP | 3290928 | 3/2018 |
| JP | 2011-047709 | 3/2011 |
| WO | WO 2008/146754 | 12/2008 |
| WO | WO 2016/175229 | 11/2016 |

OTHER PUBLICATIONS

Office Action in Europe Application No. 17199662.2, dated Dec. 6, 2019, 5 pages.

Chinese Office Action dated Jul. 29, 2021 in a counterpart Chinese patent application No. 201711066908.2.

* cited by examiner

LIQUID SEALED CARTRIDGE, METHOD FOR PRODUCING LIQUID SEALED CARTRIDGE, AND LIQUID SENDING METHOD

CROSS REFERENCE TO RELATED APPLICATIONS

This application claims priority from prior Japanese Patent Application No. 2016-216665, filed on Nov. 4, 2016, entitled "LIQUID SEALED CARTRIDGE, METHOD FOR PRODUCING LIQUID SEALED CARTRIDGE, AND LIQUID SENDING METHOD", the entire content of which is incorporated herein by reference.

FIELD OF THE INVENTION

The present invention relates to a liquid sealed cartridge, a method for producing the liquid sealed cartridge, and a liquid sending method.

BACKGROUND

As shown in FIG. 16, according to the disclosure of U.S. Patent Application Publication No. 2011/0104009, a certain amount of reagent is injected through an inlet 501 into a reagent reservoir 502 before testing, a disk 500 is rotated at a high speed, and the reagent in the reagent reservoir 502 is transferred through a narrow tube 503 into a reactor 504 due to a centrifugal force.

Further, according to the disclosure of U.S. Patent Application Publication No. 2011/0104009, after the reagent is transferred from the reagent reservoir 502 into the reactor 504, the disk 500 is put into a refrigerator to cause the reagent having been transferred into the reactor 504 to gel, and is stored.

According to U.S. Patent Application Publication No. 2011/0104009, when the disk is used for test, the disk 500 stored in the refrigerator is taken out therefrom, and the reagent having gelled in the reactor 504 is liquefied.

However, in U.S. Patent Application Publication No. 2011/0104009, when the disk 500 is taken out from the refrigerator and carried in order to use the disk 500 for test, the reagent in the reactor 504 may flow back through the narrow tube 503 into the reagent reservoir 502. If the test is performed in a state where the reagent has flowed back into the reagent reservoir 502 and is left in the reagent reservoir 502, quantification of the reagent in the reactor 504 may be degraded. Therefore, the gelling state of the reagent in the reactor 504 needs to be strictly managed.

SUMMARY OF THE INVENTION

The scope of the present invention is defined solely by the appended claims, and is not affected to any degree by the statements within this summary.

A first mode of the present invention is a liquid sealed cartridge (100, 420) in which a liquid (250) injected through an inlet (223) is previously sealed, and the liquid (250) is transferred by a centrifugal force being applied by rotation. The liquid sealed cartridge (100, 420) according to this mode includes: a liquid storage portion (210) configured to store the liquid (250); a bypass flow path (220) having one end (221) and the other end (222) connected to the liquid storage portion (210), the bypass flow path (220) having the inlet (223); and a transfer flow path (243) into which the liquid (250) is transferred from the liquid storage portion (210) when the centrifugal force is applied.

A second mode of the present invention is a method for producing a liquid sealed cartridge. The method, for producing the liquid sealed cartridge (100, 420), according to this mode includes: forming (S1) a liquid sealed cartridge (100, 420) that includes: a liquid storage portion (210) configured to store a liquid (250); and a bypass flow path (220) having one end (221) and the other end (222) connected to the liquid storage portion (210), the bypass flow path (220) having an inlet (223) through which the liquid (250) is injected; and injecting (S2) the liquid (250) through the inlet (223).

A third mode of the present invention is a liquid sending method using a liquid sealed cartridge (100, 420) that includes: a liquid storage portion (210) configured to store a liquid (250); a bypass flow path (220) having one end (221) and the other end (222) connected to the liquid storage portion (210), the bypass flow path (220) having an inlet (223) through which the liquid (250) is injected; and a transfer flow path (243) into which the liquid (250) is transferred from the liquid storage portion (210). The liquid sending method according to this mode includes transferring (S102) the liquid (250) into the transfer flow path (243) from the liquid storage portion (210) due to a centrifugal force applied by rotating the liquid sealed cartridge (100, 420).

DETAILED DESCRIPTION OF THE PREFERRED EMBODIMENTS

Embodiment 1

Figure 1A:
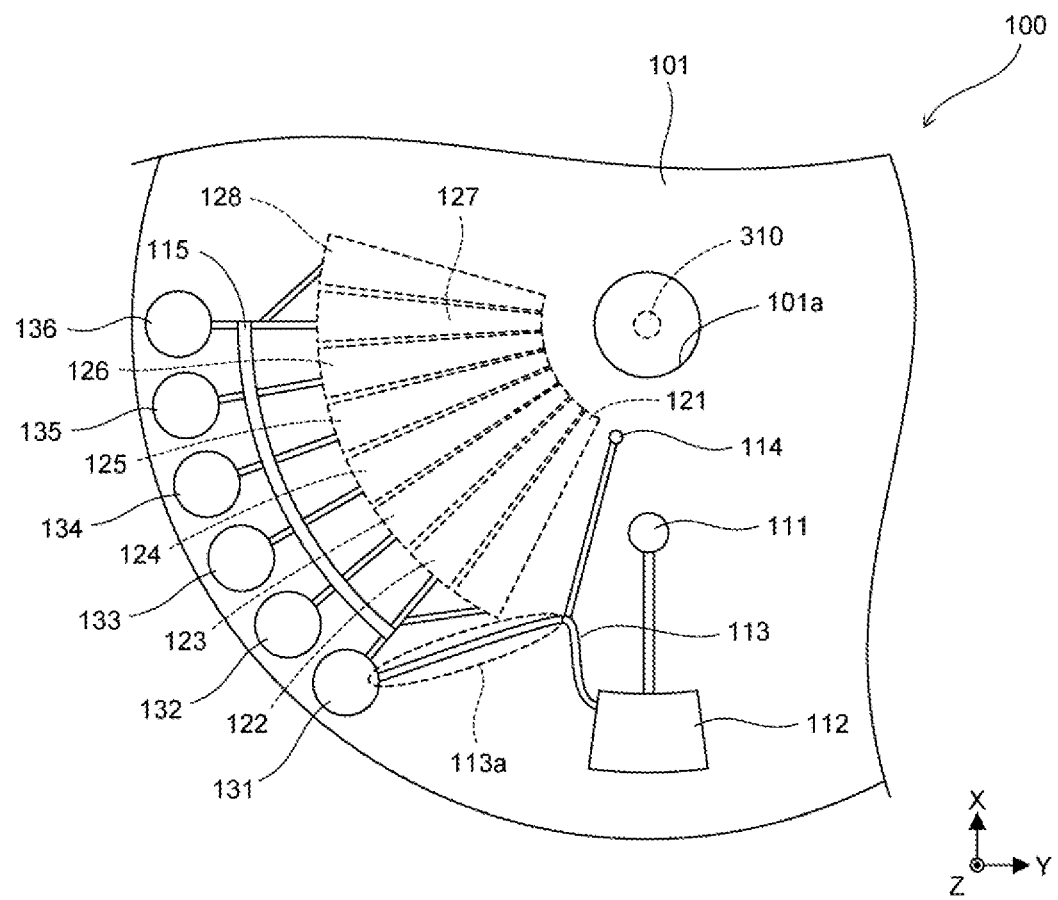
FIG. 1A is a schematic diagram illustrating a structure of a liquid sealed cartridge according to Embodiment 1.

As shown in FIG. 1A, a liquid sealed cartridge 100 is a liquid sealed cartridge in which liquid injected through an inlet is previously sealed, and the sealed liquid is transferred due to a centrifugal force applied by the cartridge being rotated. The liquid sealed cartridge 100 is a replaceable component that collectively has required functions. The liquid sealed cartridge 100 is mounted to a measurement device so as to be rotatable about a rotation shaft 310 of the measurement device. The measurement device rotates the rotation shaft 310, to rotate the liquid sealed cartridge 100 mounted thereto about the rotation shaft 310. Thus, a centrifugal force is applied to the liquid sealed cartridge 100.

FIG. 1A is a schematic diagram illustrating the liquid sealed cartridge 100 mounted to the measurement device, as viewed in the vertically upward direction from the lower side of the liquid sealed cartridge 100. In FIG. 1A, XYZ axes are orthogonal to each other. The Z-axis positive direction represents the vertically downward direction. Also in the following drawings, XYZ axes therein are the same as the XYZ axes in FIG. 1A. Hereinafter, the radial direction of a circle around the rotation shaft 310 disposed at the center of the circle is simply referred to as "radial direction". The circumferential direction of the circle around the rotation shaft 310 disposed at the center of the circle, that is, the rotating direction around the rotation shaft 310 is simply referred to as "circumferential direction".

As shown in FIG. 1A, the liquid sealed cartridge 100 includes a plate-shaped and disk-shaped substrate 101 and films 102 to 105 that cover the substrate 101. FIG. 1A shows only a part of the liquid sealed cartridge 100 for convenience, and illustration of the films 102 to 105 is omitted. The films 102 to 105 will be described below with reference to FIG. 2B, FIG. 2C, and FIG. 4B.

Components of the liquid sealed cartridge 100 are formed by the films 102, 103 described below being adhered over recesses formed in the substrate 101. The substrate 101 and the films 102, 103 are each formed from a member having a translucency. The substrate 101 has a thickness of, for example, several millimeters, and, specifically, has a thickness of 1.2 mm. The substrate 101 has a hole 101a that penetrates through the substrate 101 at the center of the substrate 101. The liquid sealed cartridge 100 is mounted to the measurement device such that the center of the hole 101a and the rotation shaft 310 of the measurement device are aligned with each other. The liquid sealed cartridge 100 may not necessarily be plate-shaped, and may include a projection or the like. The liquid sealed cartridge 100 may not necessarily be disk-shaped, and may have another shape such as a rectangular shape.

The liquid sealed cartridge 100 includes an inlet 111, a separator 112, a flow path 113, a hole 114, a flow path 115, liquid supply sections 121 to 128, and chambers 131 to 136. These components are provided in only one-third of the region of the substrate 101 as shown in FIG. 1A. However, the structure of the liquid sealed cartridge 100 is not limited thereto, and a group of the components may be provided in the remaining two-thirds of the region of the substrate 101, and three groups of the components may be provided in the substrate 101.

A specimen collected from a subject is injected through the inlet 111, and is transferred into the separator 112. The separator 112 separates the specimen into a solid component and a liquid component. The liquid component obtained by the separation by the separator 112 moves into the flow path 113. The hole 114 is formed on the inner side, of the flow path 113, in the radial direction. The liquid component positioned in a region 113a of the flow path 113 is moved into the chamber 131 due to a centrifugal force when the liquid sealed cartridge 100 is rotated. Thus, a predetermined amount of the liquid component is transferred into the chamber 131.

The liquid supply sections 121 to 128 are aligned in the circumferential direction near the inner circumference of the liquid sealed cartridge 100, and each extend along the radial direction. The liquid supply sections 121 to 128 each store liquid such as a reagent necessary for a process using the liquid sealed cartridge 100. The chambers 131 to 136 are aligned in the circumferential direction near the outer circumference of the liquid sealed cartridge 100. The liquid supply sections 122 to 127 allow the liquid contained therein to be transferred into the chambers 131 to 136, respectively, through flow paths that extend in the radial direction.

A flow path that extends outward from the liquid supply section 121 is connected to a flow path that connects between the liquid supply section 122 and the chamber 131. The liquid supply section 121 allows the liquid contained therein to be transferred into the chamber 131 through the flow path. A flow path that extends outward from the liquid supply section 128 is connected to a flow path that connects between the liquid supply section 127 and the chamber 136. The liquid supply section 128 allows the liquid contained therein to be transferred into the chamber 136 through the flow path. The flow path 115 extends in the circumferential direction, and connects between flow paths that extend inward from the chambers 131 to 136 in the radial direction.

Figure 1B:
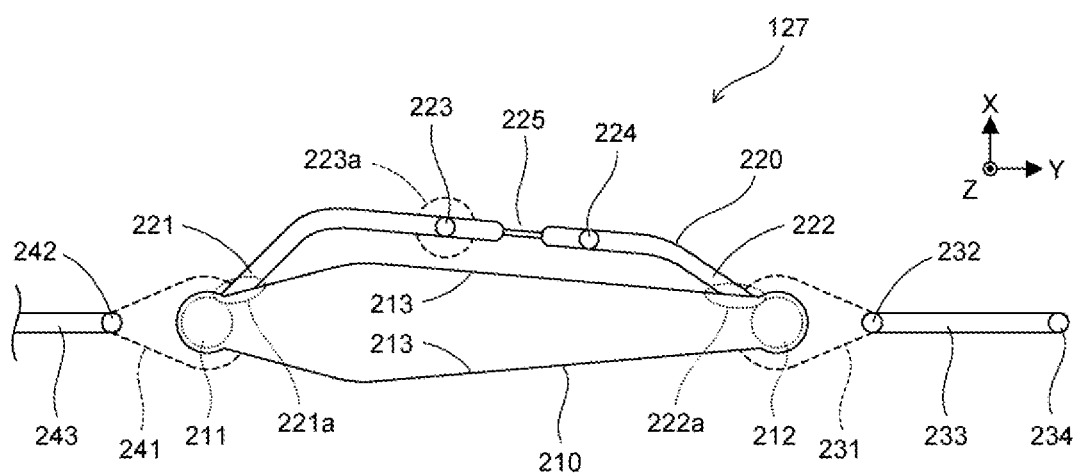
FIG. 1B is a schematic diagram illustrating a structure of a liquid supply section according to Embodiment 1.

As shown in FIG. 1B, the liquid supply section 127 includes a liquid storage portion 210, a bypass flow path 220, a recess 231, a connection flow path 232, an air introduction path 233, a hole 234, a recess 241, a connection flow path 242, and a transfer flow path 243. The liquid storage portion 210, the air introduction path 233, and the transfer flow path 243 extend along the radial direction. The rotation shaft 310 is positioned on an extension toward the hole 234 of the air introduction path 233. As shown in FIG. 1B, in the case of the liquid supply section 127, the liquid storage portion 210, the air introduction path 233, and the transfer flow path 243 extend along the Y-axis direction, and the rotation shaft 310 is positioned forward of the hole 234 in the Y-axis positive direction. The transfer flow path 243 corresponds to a flow path that extends in the radial direction in which the liquid supply section 127 and the chamber 136 are connected to each other.

The liquid supply sections 121 to 126, and 128 each have the same structure as the liquid supply section 127, and each have the components shown in FIG. 1B. The transfer flow paths 243 of the liquid supply sections 121 to 126 and 128 correspond to flow paths that extend outward from the liquid supply sections 121 to 126 and 128, respectively. Thus, since the liquid supply sections 121 to 128 have the same structure, only the structure of the liquid supply section 127 will be described below for convenience.

The liquid storage portion 210 has liquid stored therein, and has a first seal portion 211 and a second seal portion 212. The first seal portion 211 and the second seal portion 212 are provided at an end portion, of the liquid storage portion 210, on the Y-axis negative direction side and an end portion thereof on the Y-axis positive direction side, respectively. The first seal portion 211 is provided between the liquid storage portion 210 and the transfer flow path 243. The recess 231, the connection flow path 232, the air introduction path 233, and the hole 234 form an air flow path through which air is introduced into the liquid storage portion 210. The second seal portion 212 is provided between the liquid storage portion 210 and the air flow path. Specifically, the first seal portion 211 is a portion, of the substrate 101, which has a thickness reduced in the Z-axis direction, and is provided at a boundary with the recess 241 positioned on the Y-axis negative direction side of the liquid storage portion 210. The second seal portion 212 is a portion, of the substrate 101, which has a thickness reduced in the Z-axis direction, and is provided at a boundary with the recess 231 positioned on the Y-axis positive direction side of the liquid storage portion 210. The first seal portion 211 and the second seal portion 212 are provided so as to seal the inside of the liquid storage portion 210.

The first seal portion 211 is opened when the liquid in the liquid storage portion 210 is transferred into the transfer flow path 243, and a hole formed by the first seal portion 211 being opened, forms a path through which the liquid passes. The second seal portion 212 is opened when the liquid in the liquid storage portion 210 is transferred into the transfer flow path 243, and a hole formed by the second seal portion 212 being opened allows air to be introduced through the recess 231 into the liquid storage portion 210. That is, the second seal portion 212 is an introduction inlet through which air is introduced into the liquid storage portion 210 when measurement process is performed by using the liquid sealed cartridge 100.

By the first seal portion 211 and the second seal portion 212, when liquid is injected through an inlet 223, the liquid storage portion 210 can be hermetically sealed. When liquid is transferred during use, the first seal portion 211 is opened, and liquid can be thus smoothly transferred from the liquid storage portion 210 into the transfer flow path 243. When liquid is transferred during use, the second seal portion 212 is opened, and air can be thus introduced through the air flow path into the liquid storage portion 210, whereby liquid can be smoothly transferred into the transfer flow path 243 during use.

As shown in FIG. 1A, the liquid supply sections 121 to 128 are disposed so as to oppose each other in the circumferential direction. Therefore, the liquid storage portions 210 of the liquid supply sections 121 to 128 are also disposed so as to oppose each other in the circumferential direction. As shown in FIG. 1B, the liquid storage portion 210 has a pair of inner walls 213 that extend along two radial directions of a circle around the rotation shaft 310 disposed at the center of the circle. A distance, in the circumferential direction, between the paired inner walls 213 is increased outward in the radial direction. Thus, the capacity of the liquid storage portion 210 can be assuredly increased, and the liquid storage portion 210 and the bypass flow path 220 can be efficiently aligned in combination in the circumferential direction. That is, the capacity of the liquid storage portion 210 of each of the liquid supply sections 121 to 128 is assuredly increased, and the liquid supply sections 121 to 128 can be compactly disposed in the liquid sealed cartridge 100.

The bypass flow path 220 has one end 221 disposed on the Y-axis negative direction side and the other end 222 disposed on the Y-axis positive direction side. The one end 221 is disposed so as to be closer to the transfer flow path 243 than the other end 222 is. The one end 221 of the bypass flow path 220 is connected to the liquid storage portion 210 at a connection position 221a near the end portion, of the liquid storage portion 210, on the Y-axis negative direction side. The other end 222 of the bypass flow path 220 is connected to a flow path portion between the connection position 221a and the second seal portion 212. Specifically, the other end 222 is connected to the liquid storage portion 210 at a connection position 222a near the end portion, of the liquid storage portion 210, on the Y-axis positive direction side. The connection position 222a is disposed between the connection position 221a and the second seal portion 212 in the radial direction.

The bypass flow path 220 includes the inlet 223, an air opening 224, and a narrow portion 225. The inlet 223 is provided for injecting liquid into the liquid storage portion 210. The air opening 224 is provided between the other end 222 and the inlet 223, and used for discharging air in the liquid storage portion 210 and the bypass flow path 220 to the outside of the liquid sealed cartridge 100 when liquid is injected through the inlet 223. When the air opening 224 is provided between the other end 222 and the inlet 223, the inlet 223 is thus provided between the air opening 224 and the one end 221. The narrow portion 225 is provided between the inlet 223 and the air opening 224. The narrow portion 225 is a liquid stopper that allows air to pass between the inlet 223 and the air opening 224 and inhibits liquid from passing therebetween.

The bypass flow path 220 extends from the air opening 224 toward the inlet 223 in the radial direction. The bypass flow path 220 extends from the inlet 223 toward the one end 221 so as to be distant from the rotation shaft 310. The bypass flow path 220 extends from the other end 222 toward the inlet so as to be distant from the rotation shaft 310. Thus, the bypass flow path 220 extends from the other end 222 toward the one end 221 such that the bypass flow path 220 is distant from the rotation shaft 310 at any portion from the other end 222 toward the one end 221.

The bypass flow path 220 is structured to have a cross-sectional area smaller than the liquid storage portion 210. Thus, liquid injected through the inlet 223 is less likely to spread in all the directions when the liquid enters the liquid storage portion 210. Therefore, the liquid that enters the liquid storage portion 210 through the inlet 223 is inhibited from entering the end portion or the like of the liquid storage portion 210. Therefore, when the liquid is transferred during use, the liquid can be inhibited from being left in the liquid storage portion 210. For example, particularly when the liquid storage portion 210 has a complicated shape, the liquid is likely to enter the end portion of the liquid storage portion 210. However, when the bypass flow path 220 has a cross-sectional area smaller than the liquid storage portion 210, liquid is inhibited from entering the end portion of the liquid storage portion 210, whereby the liquid can be inhibited from being left in the liquid storage portion 210.

The transfer flow path 243 is provided for transferring outward the liquid in the liquid storage portion 210. The transfer flow path 243 is connected to the liquid storage portion 210 at a position that is farther from the rotation shaft 310 than the one end 221 is.

Figure 2A:
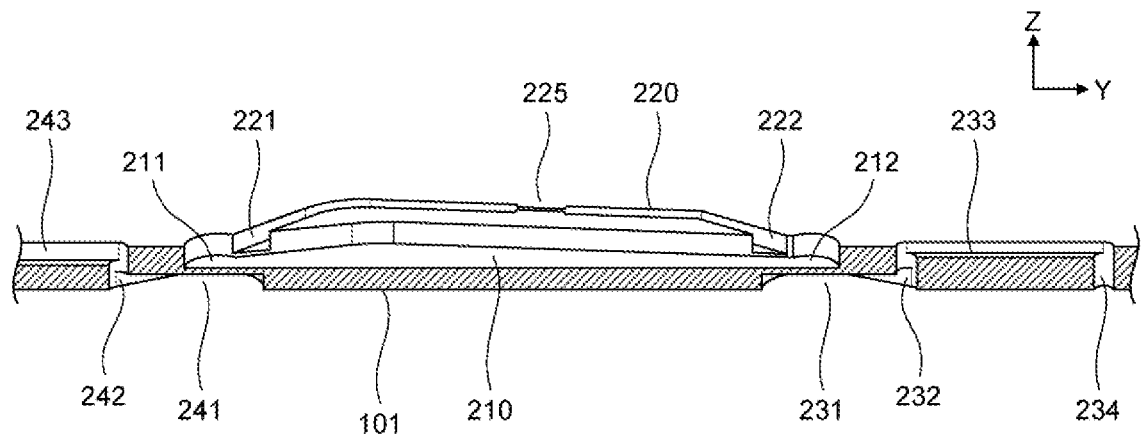
FIG. 2A is a perspective view of a cross-sectional structure of the liquid supply section according to Embodiment 1.

FIG. 2A is a perspective view schematically illustrating a structure of the liquid supply section 126 as viewed from the Z-axis positive direction side. In FIG. 2A, for convenience, the films 102, 103 are not illustrated.

As shown in FIG. 2A, the liquid storage portion 210, the bypass flow path 220, the air introduction path 233, and the transfer flow path 243 are provided on the back surface of the substrate 101 of the liquid sealed cartridge 100, that is, provided on the Z-axis positive direction side surface. The recesses 231, 241 are provided on the front surface of the substrate 101, that is, provided on the Z-axis negative direction side surface. The connection flow paths 232, 242 and the hole 234 penetrate through the substrate 101 in the Z-axis direction. The connection flow path 232 connects between the recess 231 and the air introduction path 233. The hole 234 is connected to the air introduction path 233. The connection flow path 242 connects between the recess 241 and the transfer flow path 243.

Figure 2B:
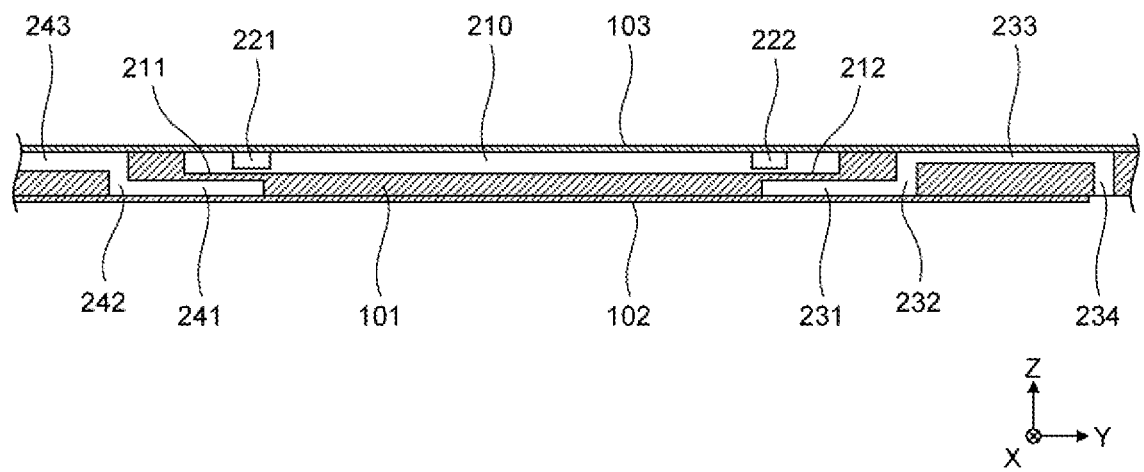
FIG. 2B is a cross-sectional view of the structure of the liquid supply section according to Embodiment 1.

As shown in FIG. 2B, the film 102 is adhered to the surface, of the substrate 101, on the Z-axis negative direction side, and the film 103 is adhered to the surface, of the substrate 101, on the Z-axis positive direction side. The film 102 is formed from a material that is deformed when the film 102 is pressed by a pressing portion 324 described below in the Z-axis positive direction. Thus, the pressing portion 324 is allowed to press the first seal portion 211 and the second seal portion 212 through the film 102 in the Z-axis positive direction. The film 102 covers the substrate 101 from a portion between the hole 234 and the connection flow path 232 to the outermost circumference of the substrate 101. Thus, the end portion, of the hole 234, on the Z-axis negative direction side is opened in the Z-axis negative direction. The film 102 is cut at positions corresponding to the inlet 223 and the air opening 224, as shown in FIG. 2C.

The film 103 is formed from a material that is less likely to be deformed such that the liquid stored in the liquid storage portion 210 is prevented from erroneously leaking to the outside. The film 103 covers the substrate 101 from the innermost circumference thereof to the outermost circumference thereof.

Figure 2C:
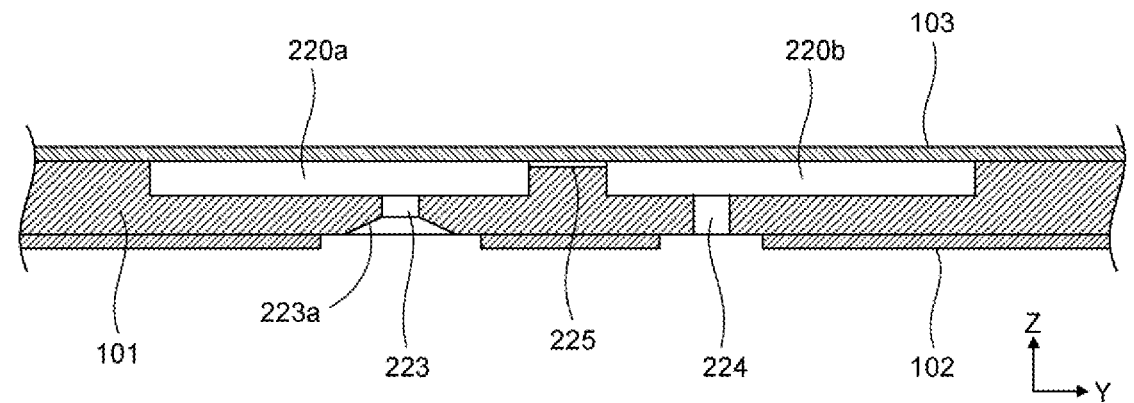
FIG. 2C is a cross-sectional view of a structure near a bypass flow path according to Embodiment 1.

As shown in FIG. 2C, the narrow portion 225 has a cross-sectional area smaller than the bypass flow path 220 between the inlet 223 and the one end 221. The inlet 223 is provided in a flow path 220a of the bypass flow path 220, and the air opening 224 is provided in a flow path 220b of the bypass flow path 220. The flow path 220a is a portion, of the bypass flow path 220, which extends in the radial direction in a portion outward of the narrow portion 225 in the radial direction. The flow path 220b is a portion, of the bypass flow path 220, which extends in the radial direction in a portion inward of the narrow portion 225 in the radial direction. The narrow portion 225 has a cross-sectional area of 0.0252 mm$^2$, the flow path 220a has a cross-sectional area of 0.306 mm$^2$, and the flow path 220b has a cross-sectional area of 0.42 mm$^2$. The inlet 223 and the air opening 224 are holes that penetrate through the substrate 101 in the Z-axis direction at the positions in the flow paths 220a, 220b, respectively. A titled portion 223a having a shape similar to that of a conical side surface is provided at the end portion, of the inlet 223, on the Z-axis negative direction side.

Next, a procedure of injecting liquid through the inlet 223 to introduce the liquid into the liquid storage portion 210 will be described with reference to FIG. 3A to FIG. 4B.

An operator who introduces liquid, prepares the liquid sealed cartridge 100 which has the films 102, 103 adhered to the substrate 101, and which does not have the films 104, 105, described below on the substrate 101. In this state, the inlet 223 and the air opening 224 of each of the liquid supply sections 121 to 128 are opened in the Z-axis negative direction as shown in FIG. 2C. Subsequently, the operator places, on a working table, the back surface side portion of the liquid sealed cartridge 100, that is, the Z-axis positive direction side portion, and the inlet 223 and the air opening 224 are caused to face upward.

Subsequently, the operator positions the tip of a pipette that contains liquid to be injected into the liquid storage portion 210, at the inlet 223 shown in FIG. 2C. The diameter of the tip of the pipette is greater than the diameter of the inlet 223 that extends in the Z-axis direction, and is less than the diameter, of the tilted portion 223a, on the Z-axis negative direction side. Thus, the tip of the pipette is positioned at the tilted portion 223a, and liquid can be smoothly injected through the inlet 223 into the flow path 220a.

Figure 3A:
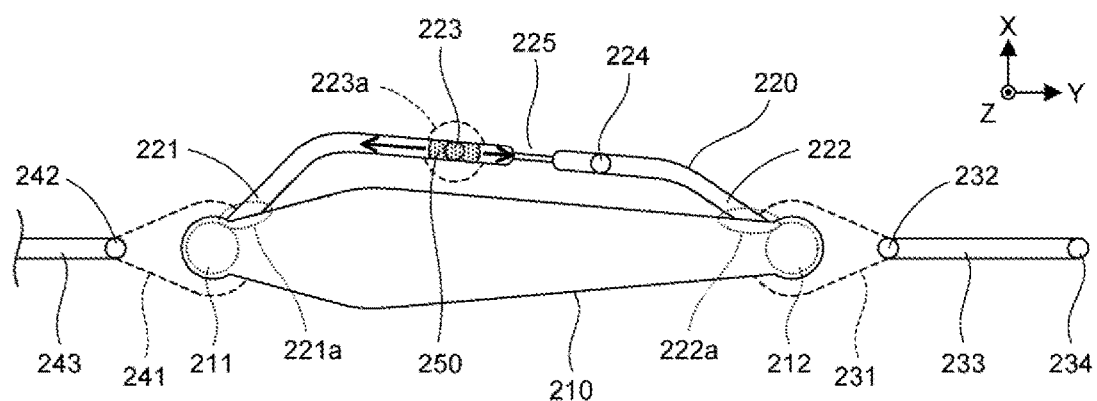
FIG. 3A illustrates a procedure of injecting liquid according to Embodiment 1.
Figure 3B:
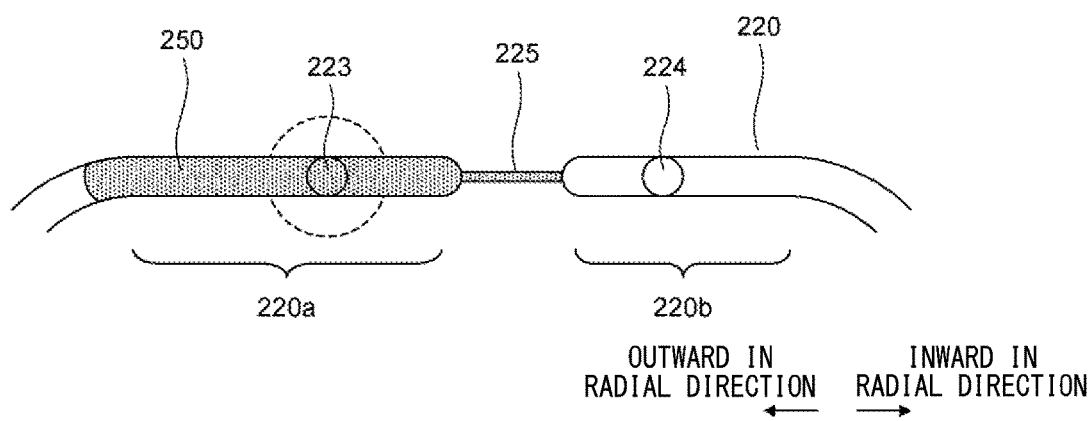
FIG. 3B illustrates an effect of a narrow portion according to Embodiment 1.

As shown in FIG. 3A, a liquid 250 injected through the inlet 223 passes through the bypass flow path 220, and spreads outward and inward of the inlet 223 in the radial direction. As shown in FIG. 2C, since the narrow portion 225 has a cross-sectional area smaller than the flow path 220a, a space through which the liquid passes is abruptly increased from the narrow portion 225 toward the end portion of the outer side portion, in the radial direction, of the flow path 220b. Thus, as shown in FIG. 3B, even when the liquid 250 reaches the end portion of the inner side portion, in the radial direction, of the narrow portion 225, the liquid 250 in the narrow portion 225 is less likely to enter the flow path 220b due to surface tension of the liquid 250. Therefore, the narrow portion 225 acts as a barrier, and the liquid 250 in the flow path 220a can be inhibited from flowing into the air opening 224 in the bypass flow path 220. Since air can pass through the narrow portion 225, in a case where the liquid in the liquid storage portion 210 is transferred into the transfer flow path 243, air is sent outward in the radial direction through the narrow portion 225, and the liquid 250 in the flow path 220a can be thus pressed outward in the radial direction.

Figure 3C:
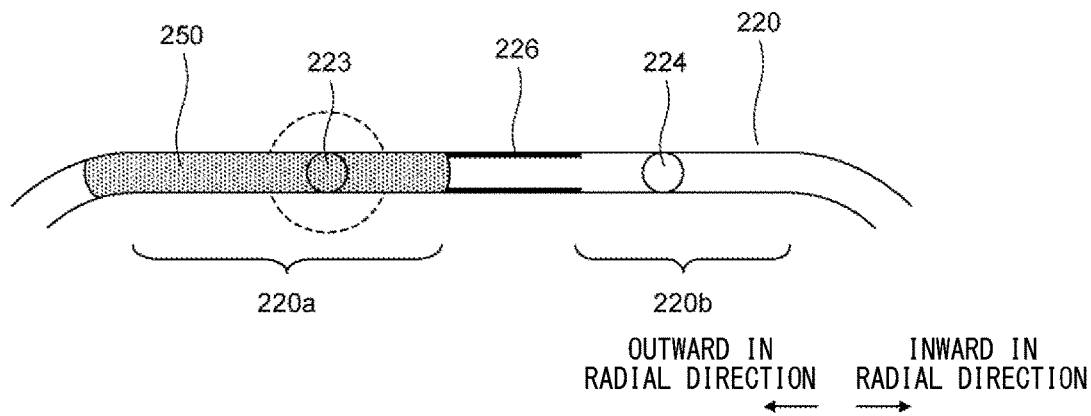
FIG. 3C illustrates an effect of a hydrophobic portion according to modification of Embodiment 1.

The liquid stopper that allows air to pass between the inlet 223 and the air opening 224 and inhibits the liquid 250 from passing therebetween is not limited to the narrow portion 225, and may have another structure. For example, as shown in FIG. 3C, the liquid stopper may be a hydrophobic portion 226 that has an inner surface having a hydrophobicity higher than the inner surface of the bypass flow path 220 between the inlet 223 and the other end 222. Unlike the narrow portion 225, the hydrophobic portion 226 shown in FIG. 3C has a cross-sectional area that is equal to the cross-sectional area of the bypass flow path 220. The hydrophobic portion 226 is formed by, for example, a hydrophobizing agent containing fluorine being applied to the inner surface. Alternatively, the hydrophobic portion 226 may be formed by a fine uneven portion being provided in the inner surface.

Also in the case shown in FIG. 3C, the hydrophobic portion 226 acts as a barrier, and the liquid 250 in the flow path 220a can be inhibited from flowing into the air opening 224. The liquid stopper can be formed by the narrow portion 225 more easily than by the hydrophobic portion 226 since the liquid stopper can be formed merely by utilizing the shape of the narrow portion 225.

The liquid stopper may include both the narrow portion and the hydrophobic portion. The liquid stopper may not be provided between the inlet 223 and the air opening 224, and a hydrophilic portion may be provided in a portion outward of the inlet 223 in the radial direction. In this case, the liquid 250 is likely to spread outward of the inlet 223 in the radial direction. Therefore, the liquid 250 can be prevented from spreading inward of the inlet 223 in the radial direction.

Figure 4A:
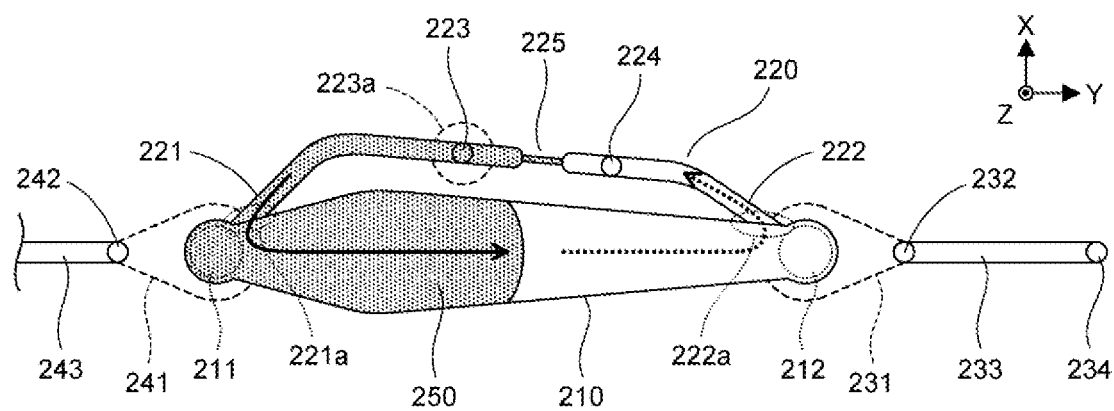
FIG. 4A illustrates a procedure of injecting liquid according to Embodiment 1.

The operator continues to inject the liquid 250 by using the pipette until a required amount of the liquid 250 is injected through the inlet 223. Thus, as shown in FIG. 4A, the liquid that has been moved from the inlet 223 to the one end 221 enters the liquid storage portion 210 at the connection position 221a, and is moved inward in the radial direction, in the liquid storage portion 210. At this time, air that has been left in the liquid storage portion 210 before injection of the liquid advances toward the other end 222 through the connection position 222a as indicated by an dotted arrow in FIG. 4A, and is discharged through the air opening 224 to the outside of the liquid sealed cartridge 100. Thus, the liquid 250 can be smoothly injected through the inlet 223.

When the liquid 250 is injected through the inlet 223, the narrow portion 225 acts as a barrier as described above, and the liquid 250 is inhibited from flowing from the inlet 223 to the air opening 224 in the bypass flow path 220. Further, by the narrow portion 225 acting as a barrier, a path from the inlet 223 to the air opening 224 is elongated, whereby the liquid 250 injected through the inlet 223 is less likely to reach the air opening 224. Thus, the liquid 250 injected through the inlet 223 can be inhibited from leaking through the air opening 224 while an operation of injecting the liquid 250 is performed.

Figure 4B:
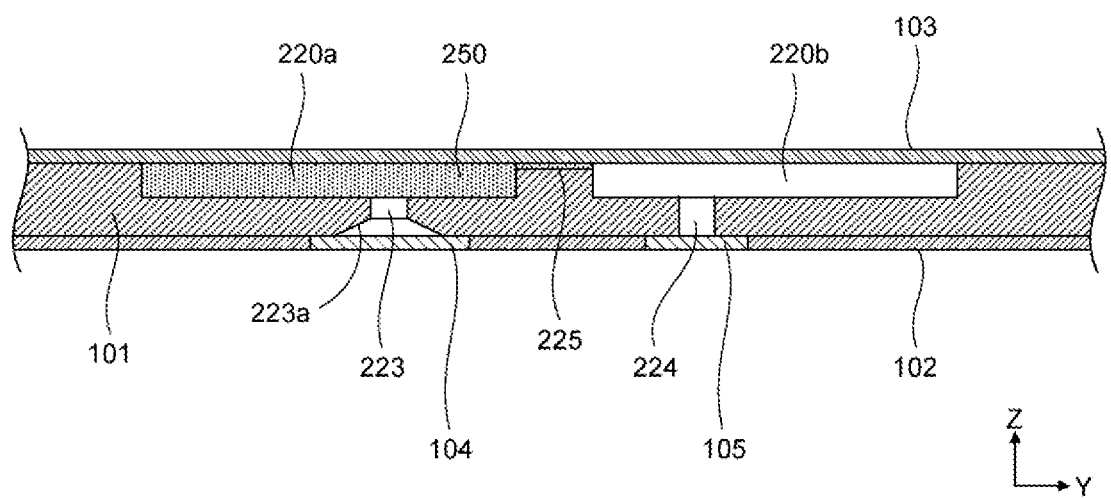
FIG. 4B is a cross-sectional view illustrating a state where an inlet and an air opening are closed, according to Embodiment 1.

When injection of the required amount of the liquid 250 is ended, the operator separates the pipette from the inlet 223, and closes the inlet 223 and the air opening 224. Specifically, as shown in FIG. 4B, the operator closes, with the film 104, an opening of the inlet 223 on the Z-axis negative direction side, and closes, with the film 105, an opening of the air opening 224 on the Z-axis negative direction side. The films 104, 105 each have a first layer formed from polyethylene terephthalate (PET) which includes an aluminium layer, and a second layer formed from linear polyethylene (L-LDPE) such that the first layer and the second layer are stacked on each other.

As shown in FIG. 4B, when the inlet 223 is closed with the film 104, the second layer of the film 104 is melted by heat, and the second layer of the film 104 is thus adhered to a portion, of the substrate 101, around the outer portion of the tilted portion 223a. Similarly, when the air opening 224 is closed with the film 105, the second layer of the film 105 is melted by heat, and the second layer of the film 105 is thus adhered to a portion, of the substrate 101, around the outer portion of the air opening 224.

Thus, the liquid 250 is injected through the inlet 223 into the liquid storage portion 210, and the inlet 223 is thereafter closed with the film 104, whereby liquid can be inhibited from leaking through the inlet 223. The liquid 250 is injected through the inlet 223 into the liquid storage portion 210, and the air opening 224 is thereafter closed with the film 105, whereby the liquid can be inhibited from leaking through the air opening 224. Although a path from the inlet 223 to the air opening 224 is long as described above, and the liquid 250 is less likely to reach the air opening 224, if, for example, the liquid 250 reaches the air opening 224 while the liquid sealed cartridge 100 is being transferred, the liquid 250 may leak through the air opening 224. However, the air opening 224 is closed after injection, and, therefore, also in this case, liquid can be inhibited from leaking through the air opening 224.

When the inlet 223 and the air opening 224 are closed with the films 104, 105, respectively, passing of air is prevented by the first layer of each of the films 104, 105. Thus, since sealing in the liquid storage portion 210 is improved, preservability of liquid in the liquid storage portion 210 is enhanced.

Thus, an operator injects a predetermined liquid into the liquid storage portion 210 of each of the liquid supply sections 121 to 128, and closes the inlet 223 and the air opening 224 of each liquid storage portion 210. Thus, the liquid sealed cartridge 100 is completed.

Figure 5A:
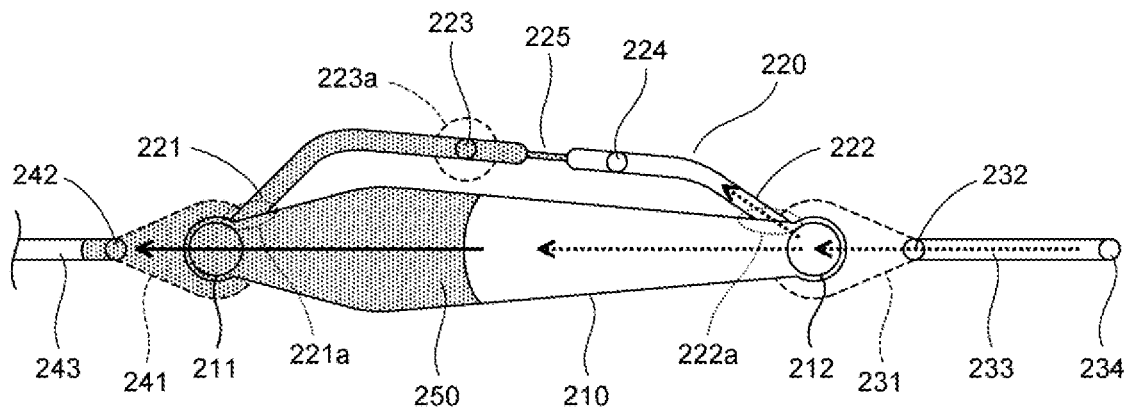
FIG. 5A illustrates a procedure of sending liquid according to Embodiment 1.
Figure 5B:
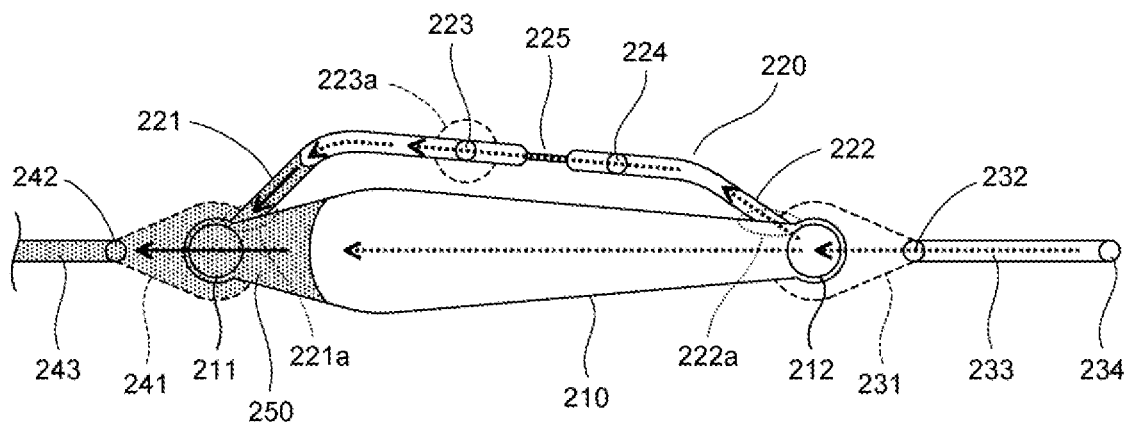
FIG. 5B illustrates a procedure of sending liquid according to Embodiment 1.
Figure 5C:
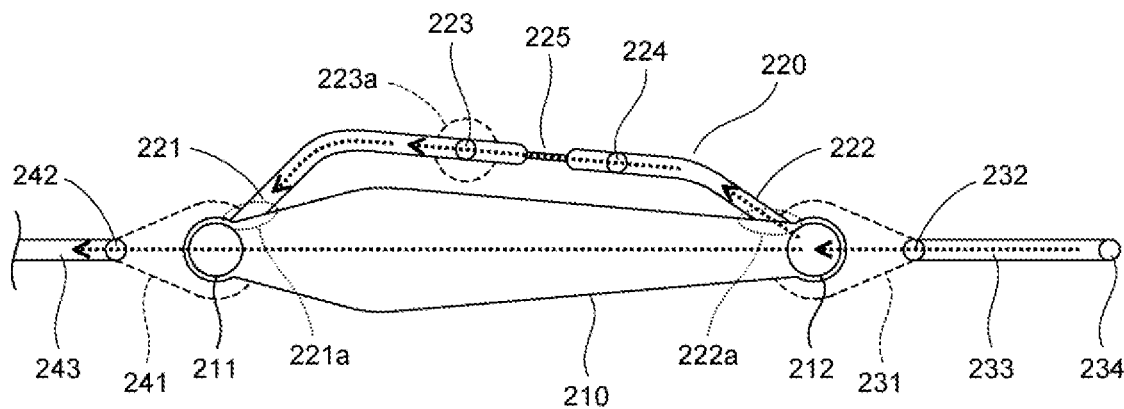
FIG. 5C illustrates a procedure of sending liquid according to Embodiment 1.

Next, a procedure of transferring the liquid in the liquid storage portion 210, into the transfer flow path 243, in the measurement operation will be described with reference to FIG. 5A to FIG. 5C.

When an operator uses a measurement device to perform measurement, the operator sets the completed liquid sealed cartridge 100 in the measurement device in advance such that the surface, of the liquid sealed cartridge 100, on the Z-axis positive direction side faces vertically downward, and starts the measurement operation. In the measurement device, the pressing portion 324 described below is driven to press the first seal portion 211 and the second seal portion 212 through the film 102 in the Z-axis positive direction, thereby opening the first seal portion 211 and the second seal portion 212. Thus, the inner side portion, of the liquid storage portion 210, in the radial direction is connected to the recess 231, and the outer side portion, of the liquid storage portion 210, in the radial direction is connected to the recess 241.

Subsequently, the measurement device rotates the liquid sealed cartridge 100 around the rotation shaft 310, and causes a centrifugal force to be applied to the liquid sealed cartridge 100. Thus, the liquid 250 in the liquid storage portion 210 is moved outward in the radial direction, as shown in FIG. 5A. At this time, air taken in through the hole 234 enters the liquid storage portion 210 through a hole formed by the second seal portion 212 being opened as indicated by a dotted arrow in FIG. 5A.

A part of air taken in through the second seal portion 212 into the liquid storage portion 210 advances in the liquid storage portion 210, and presses, together with the centrifugal force, the liquid 250 in the liquid storage portion 210 outward in the radial direction. Thus, as shown in FIG. 5B, the liquid 250 in the liquid storage portion 210 passes, through a hole formed by the first seal portion 211 being opened, in the recess 241 and the connection flow path 242, and is transferred into the transfer flow path 243.

A part of air taken at the position of the second seal portion 212 into the liquid storage portion 210 advances in the bypass flow path 220. Air taken through the other end 222 into the bypass flow path 220 passes through the narrow portion 225, and presses, together with the centrifugal force, the liquid 250 in the bypass flow path 220 toward the one end 221. Thus, as shown in FIG. 5B, the liquid 250 in the bypass flow path 220 passes through the one end 221, and is sent outward of the liquid storage portion 210 in the radial direction, and is transferred into the transfer flow path 243 similarly to the liquid 250 in the liquid storage portion 210.

Thus, when the liquid 250 is transferred due to the centrifugal force, air is introduced through the position of the second seal portion into both the liquid storage portion 210 and the other end 222 of the bypass flow path 220. Therefore, the liquid 250 in the bypass flow path 220 flows through the one end 221 of the bypass flow path 220 into the liquid storage portion 210 due to the centrifugal force, and is further transferred together with the liquid 250 in the liquid storage portion 210. Therefore, as shown in FIG. 5C, the liquid 250 can be prevented from being left in the liquid storage portion 210 and the bypass flow path 220. Thus, a predetermined amount of liquid can be appropriately transferred into the transfer flow path 243.

The one end 221 and the other end 222 of the bypass flow path 220 are connected to the liquid storage portion 210. Thus, even if, at a point of time when use of the liquid sealed cartridge 100 is started, the liquid 250 in the liquid storage portion 210 has moved into the bypass flow path 220, both the liquid 250 in the liquid storage portion 210 and the liquid in the bypass flow path 220 can be transferred into the transfer flow path 243 by a centrifugal force being applied to the liquid sealed cartridge 100 during use. Therefore, the liquid 250 injected through the inlet 223 is inhibited from being left in the liquid storage portion 210 and the bypass flow path 220 during use, and a predetermined amount of the liquid 250 can be appropriately transferred into the transfer flow path 243.

The bypass flow path 220 extends from the inlet 223 toward the one end 221 so as to be distant from the rotation shaft 310. Thus, when a centrifugal force is applied, the liquid 250 is less likely to be left between the inlet 223 and the one end 221. Therefore, the liquid 250 in the bypass flow path 220 can be smoothly transferred into the liquid storage portion 210 due to the centrifugal force.

The bypass flow path 220 may extend from the inlet 223 toward the one end 221 in the circumferential direction of a circle around the rotation shaft 310 disposed at the center of the circle. In this case, by a high centrifugal force being applied to the liquid sealed cartridge 100, the liquid 250 in the bypass flow path 220 can be transferred into the liquid storage portion 210. A part, of the bypass flow path 220, between the inlet 223 and the one end 221 may extend toward the rotation shaft 310. In this case, a speed at which the liquid sealed cartridge 100 is rotated is changed at predetermined time intervals, to generate Euler force in the rotating direction, whereby the liquid 250 in the bypass flow path 220 can be transferred into the liquid storage portion 210.

However, in a case where the bypass flow path 220 extends from the inlet 223 toward the one end 221 in the circumferential direction of the circle around the rotation shaft 310 disposed at the center of the circle, or extends from the inlet 223 toward the one end 221 so as to be distant from the rotation shaft 310, the liquid 250 can be inhibited from being left between the inlet 223 and the one end 221 when a centrifugal force is applied, with enhanced effectiveness. Further, in a case where the bypass flow path 220 extends from the inlet 223 toward the one end 221 so as to be distant from the rotation shaft 310, the liquid 250 can be inhibited from being left in the bypass flow path 220, with enhanced effectiveness.

The bypass flow path 220 extends from the other end 222 toward the inlet 223 so as to be distant from the rotation shaft 310. Thus, liquid is less likely to be left between the inlet 223 and the other end 222 when a centrifugal force is applied, whereby the liquid 250 in the bypass flow path 220 can be smoothly transferred into the liquid storage portion 210 due to the centrifugal force. For example, even in a case where the liquid 250 in the liquid storage portion 210 enters a portion, of the bypass flow path 220, between the inlet 223 and the other end 222 when the liquid sealed cartridge 100 is conveyed, the liquid 250 can be smoothly transferred into the liquid storage portion 210 due to a centrifugal force.

Similarly to a portion, of the bypass flow path 220, between the inlet 223 and the one end 221 as described above, the bypass flow path 220 may extend from the other end 222 toward the inlet 223 in the circumferential direction of a circle around the rotation shaft 310 disposed at the center of the circle. A portion, the bypass flow path 220, between the other end 222 and the inlet 223 may extend toward the rotation shaft 310.

Next, a structure of a measurement device 300 will be described.

Figure 6:
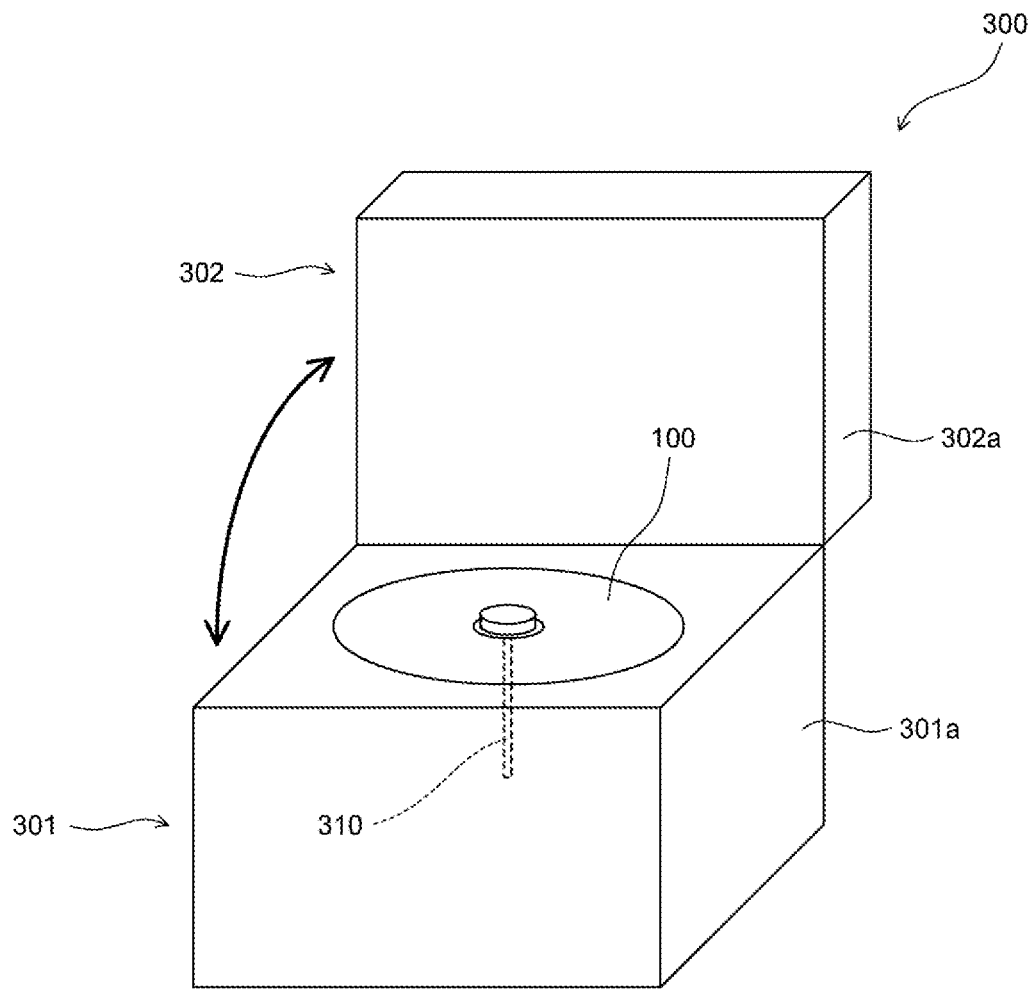
FIG. 6 is a schematic diagram illustrating a structure of a measurement device according to Embodiment 1.
Figure 6:
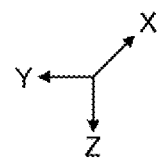

As shown in FIG. 6, the measurement device 300 includes a body portion 301 and a lid portion 302. Portions, of the body portion 301, other than a portion opposing the lid portion 302 are covered by a casing 301a. Portions, of the lid portion 302, other than a portion opposing the body portion 301 are covered by a casing 302a. The body portion 301 supports the lid portion 302 such that the lid portion 302 is openable and closable. When the liquid sealed cartridge 100 is attached or detached, the lid portion 302 is opened as shown in FIG. 6. The liquid sealed cartridge 100 is mounted to the upper portion of the body portion 301. The body portion 301 includes the rotation shaft 310 that extends parallel to the Z-axis direction. The measurement device 300 rotates the liquid sealed cartridge 100 having been mounted thereto, around the rotation shaft 310.

The measurement device 300 is an immune analyzer that uses the liquid sealed cartridge 100 to separate a plasma component from a blood specimen, detect a test substance in the plasma component by using antigen-antibody reaction, and analyze the test substance on the basis of the detection result.

Figure 7:
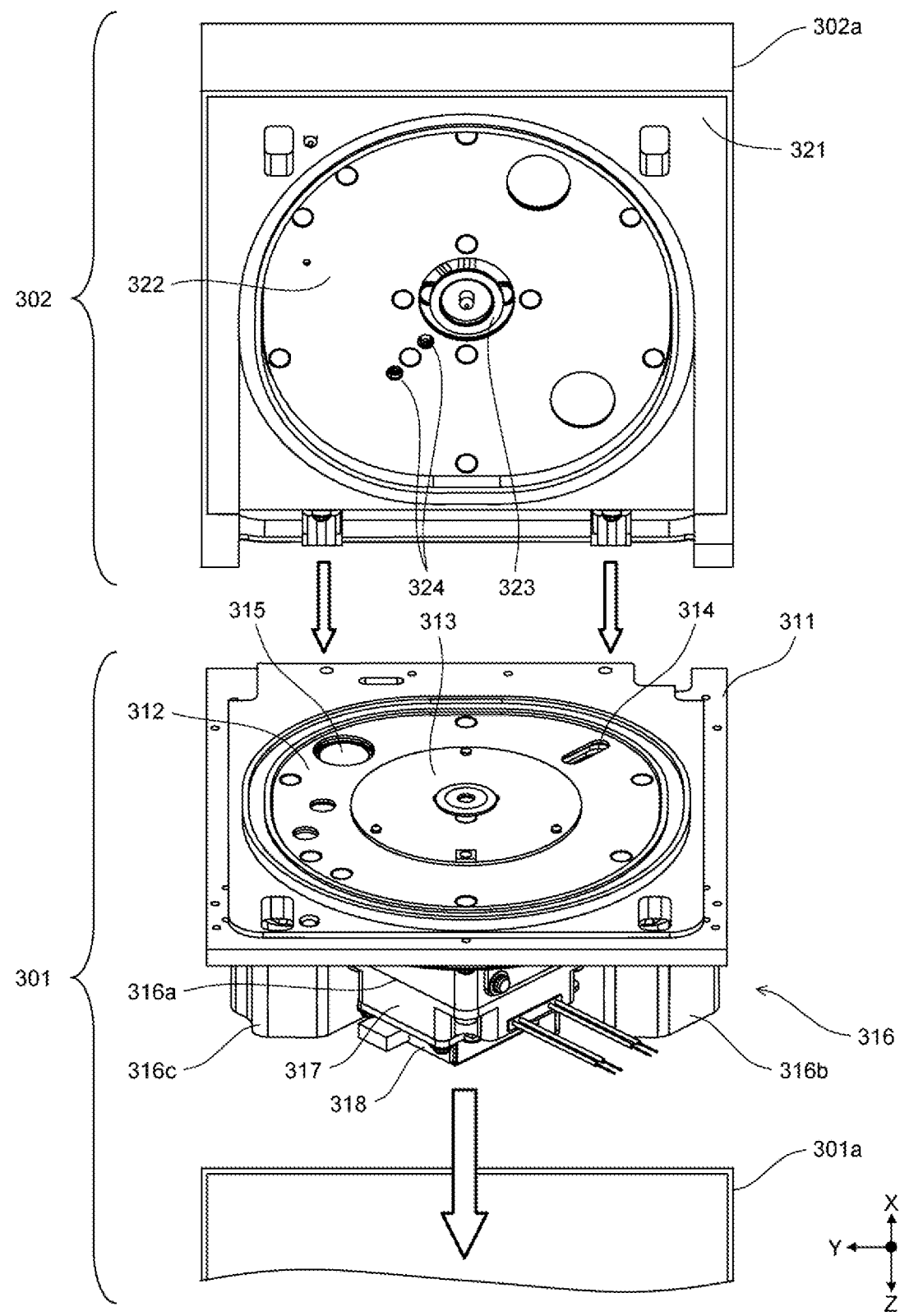
FIG. 7 illustrates a structure of a body portion of the measurement device as viewed from diagonally above the body portion, according to Embodiment 1, and illustrates a structure of a lid portion as viewed from diagonally below the lid portion, according to Embodiment 1.

As shown in FIG. 7, the body portion 301 includes a mounting member 311, a plate member 312, a support member 313, a magnetic force application section 314, a detector 315, a housing unit 316, a motor 317, and an encoder 318.

The mounting member 311 is shaped so as to be fitted into the casing 301a. The plate member 312 is disposed at the center of the upper surface of the mounting member 311. The plate member 312 is formed from a metal having a high thermal conductivity. A heater 331 described below is mounted on the lower surface of the plate member 312. The support member 313 is mounted to the center of the mounting member 311 through a mounting member 319 described below. The support member 313 is implemented by, for example, a turn table.

The magnetic force application section 314 is mounted on the lower surface of the mounting member 311 so as to oppose the lower surface of the liquid sealed cartridge 100 placed on the support member 313 through holes formed in the mounting member 311 and the plate member 312. The magnetic force application section 314 includes a magnet, and a mechanism for moving the magnet in the Z-axis direction and the radial direction. The detector 315 is mounted on the lower surface of the mounting member 311 so as to oppose the lower surface of the liquid sealed cartridge 100 placed on the support member 313 through holes formed in the mounting member 311 and the plate member 312. The detector 315 includes a light detector. The light detector of the detector 315 optically detects a test substance stored in the chamber 136. The light detector of the detector 315 is implemented by, for example, a photomultiplier, a phototube, a photodiode, or the like.

The housing unit 316 is mounted on the lower surface of the mounting member 311. The housing unit 316 includes a lower surface 316a and housings 316b, 316c. A hole 316d described below is formed at the center of the upper surface of the housing unit 316. The hole 316d penetrates in the up-down direction from the upper surface of the housing unit 316 to the lower surface 316a. The rotation shaft 310 passes through the hole 316d. The housings 316b, 316c are formed as recesses that are recessed downward from the upper surface of the housing unit 316. The magnetic force application section 314 and the detector 315 are housed in the housings 316b, 316c, respectively. The motor 317 is implemented as a stepping motor. The motor 317 is mounted on the lower surface 316a, and causes the rotation shaft 310 to rotate around the Z-axis. The encoder 318 is mounted on the lower surface of the motor 317, and detects the rotation of a drive shaft 317a, of the motor 317, described below.

FIG. 7 illustrates the lid portion 302 as viewed from therebelow. The lid portion 302 includes a mounting member 321, a plate member 322, a clamper 323, and two pressing portions 324.

The mounting member 321 is shaped so as to be fitted into the casing 302a. The plate member 322 is disposed at the center of the lower surface of the mounting member 321. The plate member 322 is formed form a metal having a high thermal conductivity, similarly to the plate member 312. A heater 332 described below is mounted on the upper surface of the plate member 322. The clamper 323 is mounted at the center of the mounting member 321. The two pressing portions 324 are mounted on the upper surface of the mounting member 321. The two pressing portions 324 are aligned in the radial direction of the liquid sealed cartridge 100 placed on the support member 313, when the lid portion 302 is closed. By the two pressing portions 324, the first seal portion 211 and the second seal portion 212 are pressed from thereabove through holes formed in the mounting member 321 and the plate member 322, and the first seal portion 211 and the second seal portion 212 are opened by the pressing force.

When the measurement device 300 is assembled, the mounting member 311 and the housing unit 316 that are assembled as shown in FIG. 7 are mounted in the casing 301a, to complete the body portion 301. The lid portion 302 assembled as shown in FIG. 7 is mounted so as to be openable and closable relative to the mounting member 311 of the body portion 301, whereby the lid portion 302 is mounted to the body portion 301. Thus, the measurement device 300 is completed.

Figure 8:
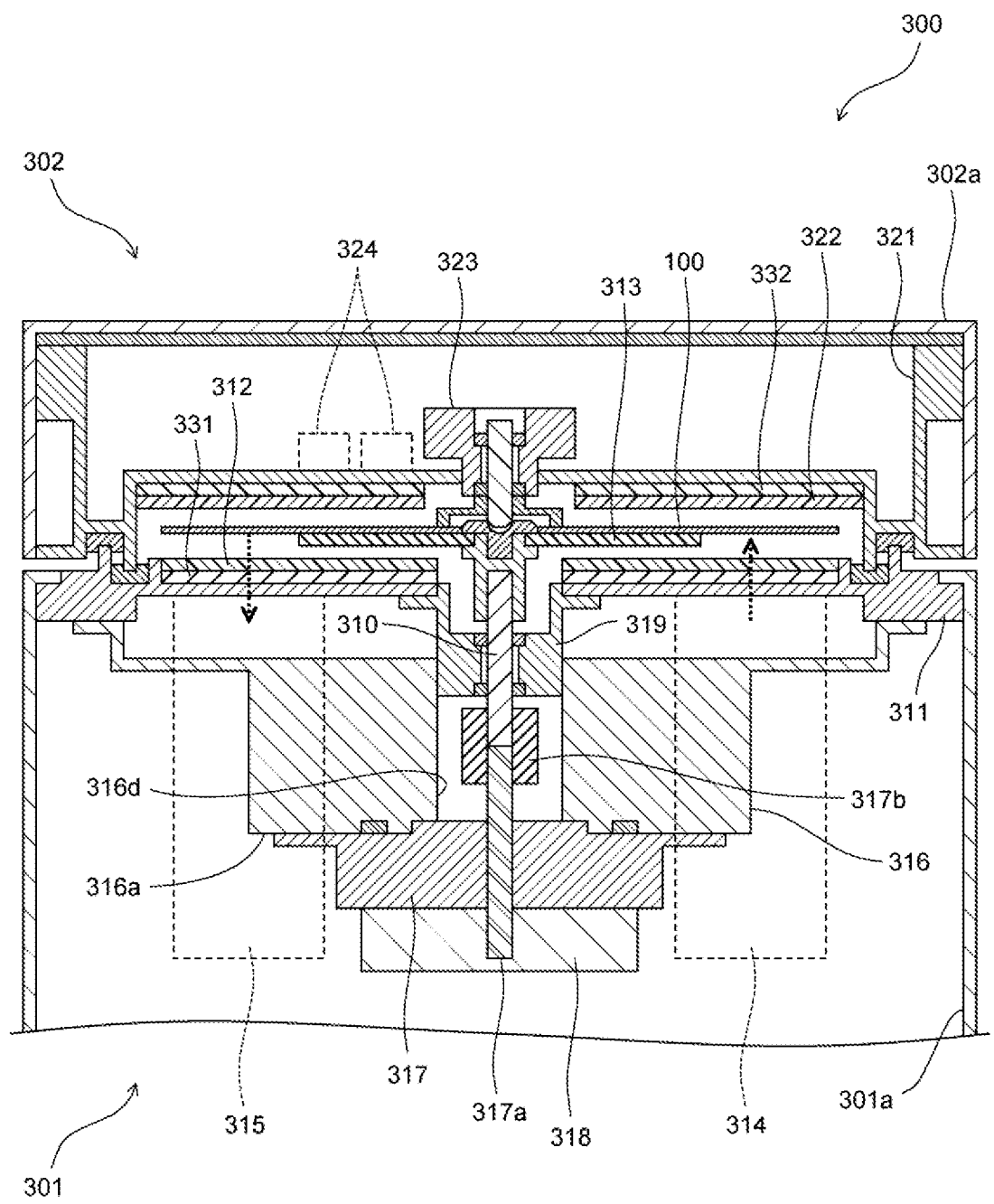
FIG. 8 is a schematic diagram illustrating a cross-section, of the measurement device, which is cut at the plane parallel to a YZ-plane that passes through a rotation shaft, as viewed from the lateral side, according to Embodiment 1.

FIG. 8 is a schematic diagram illustrating a cross-section, of the measurement device 300, which is cut at the plane parallel to the YZ-plane that passes through the rotation shaft 310. FIG. 8 illustrates a state where the liquid sealed cartridge 100 is mounted to the measurement device 300 and the lid portion 302 is closed. As described above, the magnetic force application section 314 and the detector 315 are mounted on the lower surface of the mounting member 311, and the two pressing portions 324 are mounted on the upper surface of the mounting member 321. In FIG. 8, positions corresponding to positions at which the components, respectively, are disposed are indicated by dashed lines.

As shown in FIG. 8, the drive shaft 317a of the motor 317 extends into the hole 316d. The mounting member 319 is mounted at the upper portion of the hole 316d. The mounting member 319 supports the rotation shaft 310 that extends in the up-down direction such that the rotation shaft 310 is rotatable. The rotation shaft 310 is fixed, in the hole 316d, to the drive shaft 317a of the motor 317 by a fixing member 317b.

The support member 313 for supporting the lower surface of the liquid sealed cartridge 100 is fixed through a predetermined member to the upper portion of the rotation shaft 310. When the motor 317 is driven and the drive shaft 317a is rotated, a rotation driving force is transmitted to the support member 313 through the rotation shaft 310. Thus, the liquid sealed cartridge 100 placed on the support member 313 is rotated about the rotation shaft 310. When the liquid sealed cartridge 100 is placed on the support member 313 and the lid portion 302 is closed, the clamper 323 presses the inner circumferential portion of the upper surface of the liquid sealed cartridge 100 such that the liquid sealed cartridge 100 is rotatable.

Figure 9:
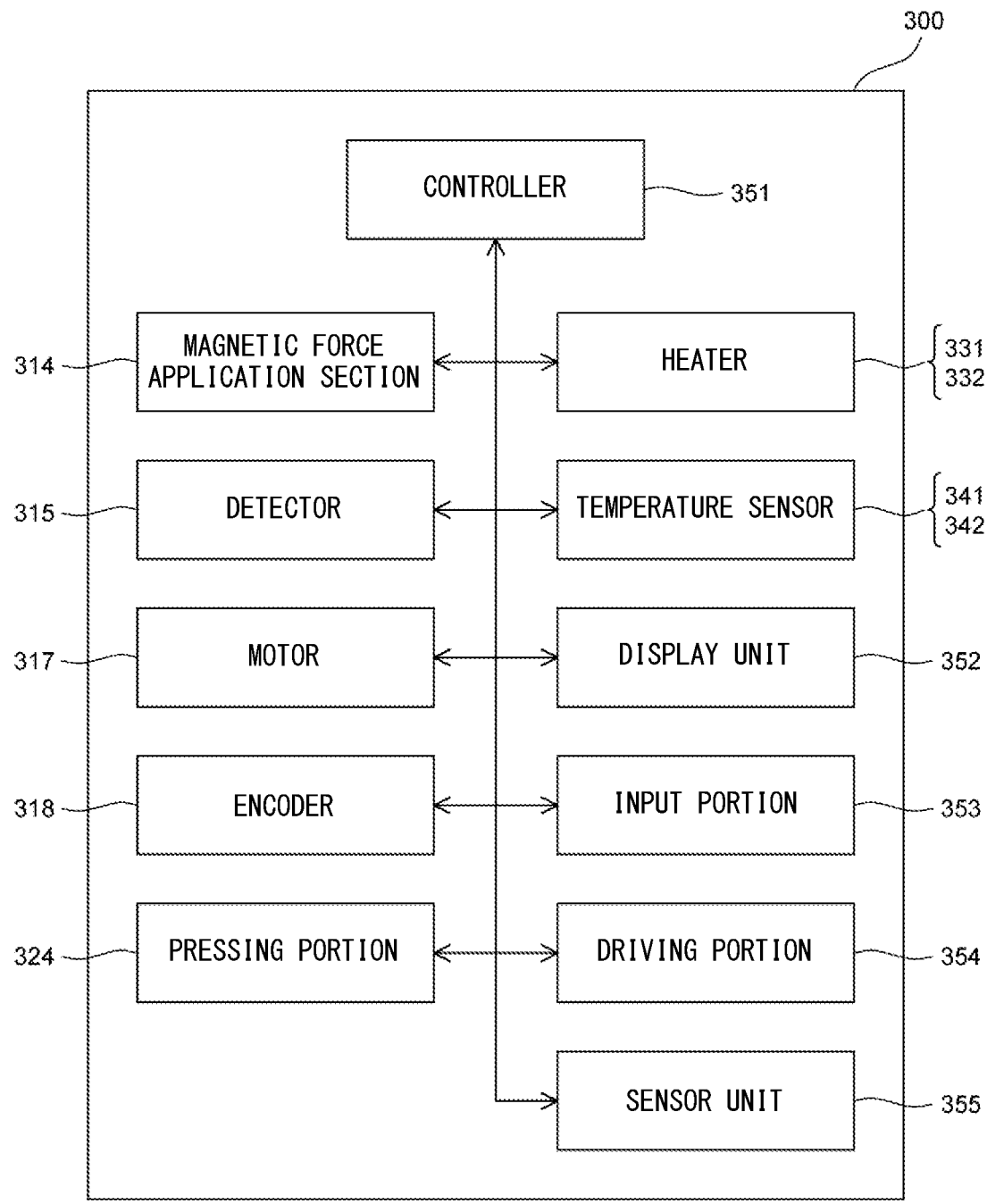
FIG. 9 is a block diagram illustrating a structure of the measurement device according to Embodiment 1.

The heater 331 is mounted on the lower surface of the plate member 312, and the heater 332 is mounted on the upper surface of the plate member 322. In the heaters 331, 332, a heat generating surface is a plane, and the heat generating surface is disposed so as to be parallel to the liquid sealed cartridge 100. Thus, the liquid sealed cartridge 100 can be efficiently heated. Temperature sensors 341, 342 shown in FIG. 9 are disposed at the plate members 312, 322, respectively. The temperature sensors 341, 342 detect temperatures of the plate members 312, 322, respectively. A controller 351 described below drives the heaters 331, 332 such that the temperature, of the plate member 312, detected by the temperature sensor 341 and the temperature, of the plate member 322, detected by the temperature sensors 342 are predetermined temperatures in the measurement.

The magnetic force application section 314 applies a magnetic force to the liquid sealed cartridge 100 by using a magnet as indicated by a dotted upward arrow in FIG. 8. The detector 315 receives light generated from the chamber 136 of the liquid sealed cartridge 100 as indicated by a dotted downward arrow in FIG. 8. When the lid portion 302 is closed, passing of light is prevented between the outside and a space in which the liquid sealed cartridge 100 is disposed. Thus, since light does not enter, from the outside, the space in which the liquid sealed cartridge 100 is disposed, even when light generated in the reaction in the chamber 136 is very low, light generated in reaction can be accurately detected by the light detector of the detector 315.

As shown in FIG. 9, the measurement device 300 includes the magnetic force application section 314, the detector 315, the motor 317, the encoder 318, the pressing portion 324, the heaters 331, 332, the temperature sensors 341, 342, the controller 351, a display unit 352, an input portion 353, a driving portion 354, and a sensor unit 355.

The controller 351 includes, for example, a processing unit and a storage unit. The processing unit includes, for example, a CPU, an MPU, and the like. The storage unit is implemented as, for example, a flash memory, a hard disk, or the like. The controller 351 receives signals from the components, respectively, of the measurement device 300, and controls the components of the measurement device 300. The display unit 352 and the input portion 353 are provided in, for example, a side surface portion of the body portion 301 or an upper surface portion of the lid portion 302. The display unit 352 is implemented as, for example, a liquid crystal panel. The input portion 353 is implemented as, for example, a button or a touch panel. The driving portion 354 includes another mechanism disposed in the measurement device 300. The sensor unit 355 includes a sensor for detecting a predetermined portion of the liquid sealed cartridge 100 mounted on the support member 313, and another sensor disposed in the measurement device 300.

Figure 10:
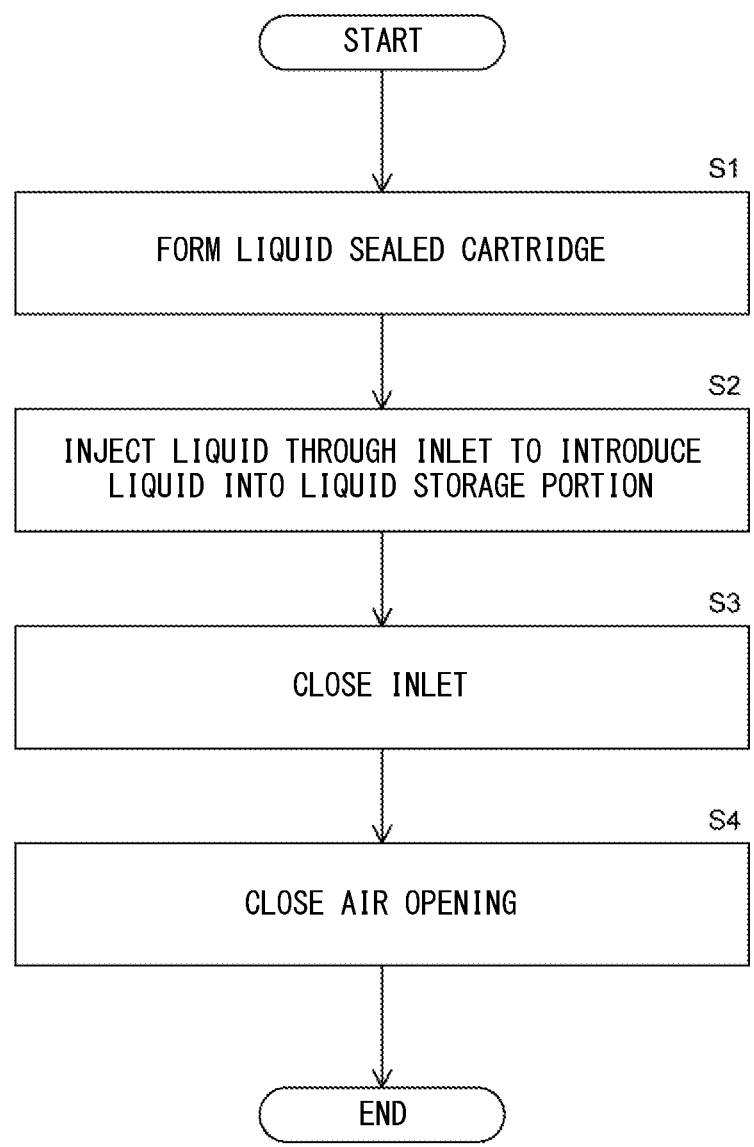
FIG. 10 is a flow chart showing a method for producing the liquid sealed cartridge according to Embodiment 1.

Next, a method for producing the liquid sealed cartridge 100 will be described with reference to FIG. 10.

In step S1, an operator who introduces liquid forms the liquid sealed cartridge 100. Specifically, the operator forms the substrate 101 by injection molding or the like, and adheres the films 102, 103 to the formed substrate 101. Thus, the liquid sealed cartridge 100 which has the substrate 101 to which the films 104, 105 have not been adhered, is formed. The operator places, on a working table, the back surface side portion of the liquid sealed cartridge 100, that is, the Z-axis positive direction side portion thereof, and causes the inlet 223 and the air opening 224 to face upward.

In step S2, the operator injects liquid through the inlet 223, to introduce the liquid into the liquid storage portion 210. Specifically, the operator injects an R1 reagent through the inlet 223 of the liquid supply section 121, to introduce the R1 reagent into the liquid storage portion 210 of the liquid supply section 121. The operator injects an R2 reagent through the inlet 223 of the liquid supply section 122, to introduce the R2 reagent into the liquid storage portion 210 of the liquid supply section 122. The operator injects an R3 reagent through the inlet 223 of the liquid supply section 123, to introduce the R3 reagent into the liquid storage portion 210 of the liquid supply section 123. The operator injects washing liquid through the inlet 223 of each of the liquid supply sections 124 to 126, to introduce the washing liquid into the liquid storage portion 210 of each of the liquid supply sections 124 to 126. The operator injects an R4 reagent through the inlet 223 of the liquid supply section 127, to introduce the R4 reagent into the liquid storage portion 210 of the liquid supply section 127. The operator injects an R5 reagent through the inlet 223 of the liquid supply section 128, to introduce the R5 reagent into the liquid storage portion 210 of the liquid supply section 128. The R1 to R5 reagents and the washing liquid will be described below in the description for an operation of the measurement device 300.

In step S3, the operator closes the inlet 223 after the liquid has been stored in the liquid storage portion 210. Specifically, the inlet 223 of each of the liquid supply sections 121 to 128 is closed with the film 104. Thus, liquid can be inhibited from leaking through the inlet 223. In step S4, the operator closes the air opening 224. Specifically, the air opening 224 of each of the liquid supply sections 121 to 128 is closed with the film 105. Thus, liquid can be inhibited from leaking through the air opening 224.

Thus, the production of the liquid sealed cartridge 100 is ended. A case where the procedure shown in FIG. 10 is performed by an operator is described above. However, the procedure shown in FIG. 10 may be automatically performed by a production device.

Next, an operation performed by the measurement device 300 will be described with reference to FIG. 11.

Firstly, an operator who performs measurement by using the measurement device 300, injects a blood specimen collected from a subject, through the inlet 111, and places the liquid sealed cartridge 100 on the support member 313 of the measurement device 300. The operator operates the input portion 353, to start measurement using the measurement device 300.

A test substance in the blood specimen includes, for example, an antigen. The antigen is, for example, Hepatitis B surface antigen (HBsAg). The test substance may be one or more of an antigen, an antibody, and protein.

In the following control, the controller 351 obtains a rotational position of the drive shaft 317a of the motor 317 on the basis of an output signal from the encoder 318 connected to the motor 317. The controller 351 causes a sensor to detect a predetermined portion of the rotating liquid sealed cartridge 100, to obtain a position of the liquid sealed cartridge 100 in the rotating direction. Alternatively, the liquid sealed cartridge 100 may be mounted at a predetermined position on the support member 313. Thus, the controller 351 causes each component of the liquid sealed cartridge 100 to be positioned at a predetermined position in the rotating direction.

Figure 11:
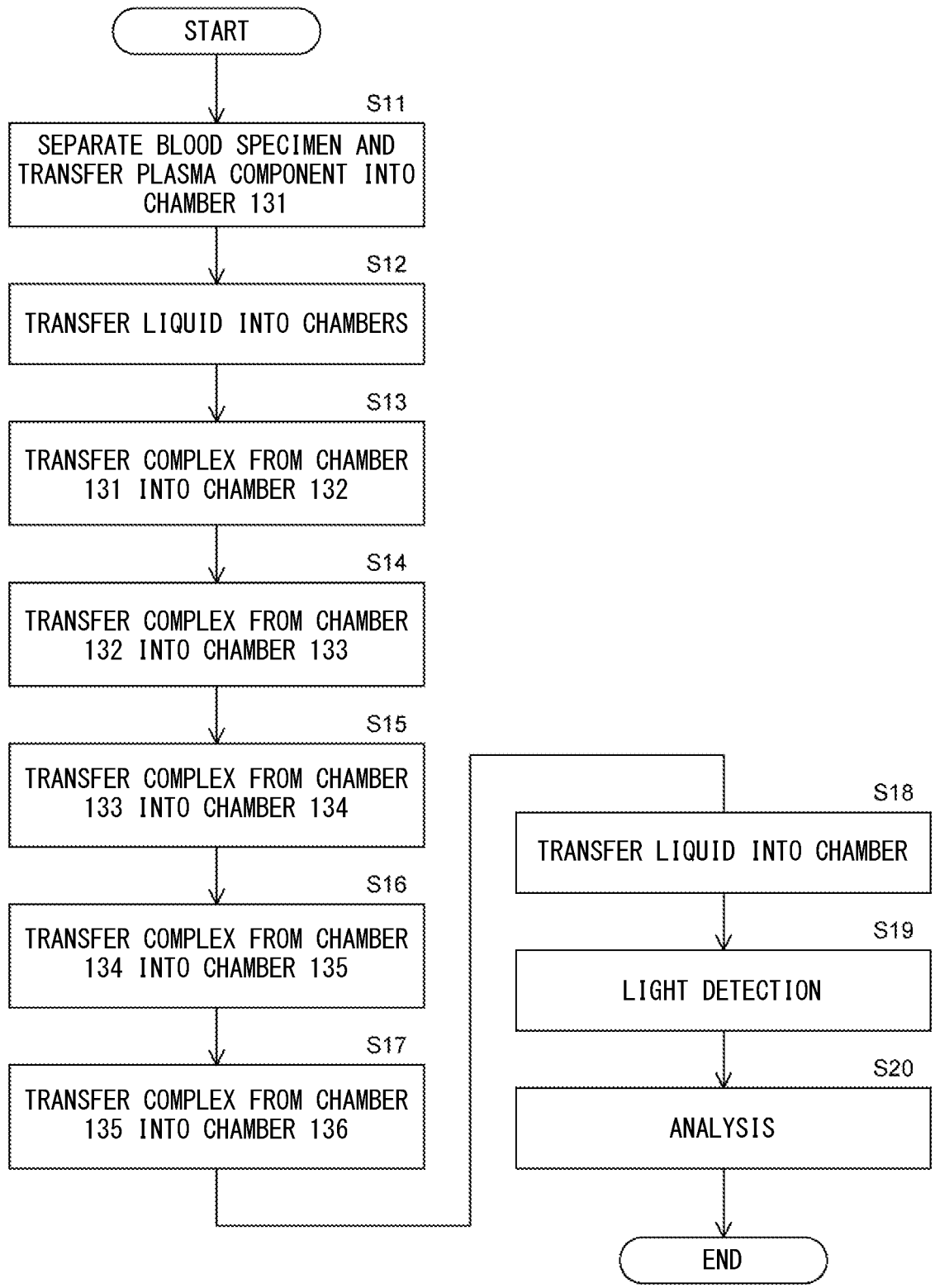
FIG. 11 is a flow chart showing a measurement operation performed by the measurement device according to Embodiment 1.

When the controller 351 receives an instruction for start from an operator through the input portion 353, the controller 351 starts the process shown in FIG. 11. In step S11, the controller 351 causes a plasma component that is contained in the blood specimen injected through the inlet 111 to be transferred into the chamber 131. Specifically, the controller 351 drives the motor 317 to rotate the liquid sealed cartridge 100 such that the blood specimen is separated into a blood cell component and a plasma component in the separator 112. The controller 351 waits for a predetermined time period until the flow path 113 is filled with the plasma component. Thereafter, the controller 351 drives the motor 317 to rotate the liquid sealed cartridge 100 such that the plasma component positioned in the region 113a of the flow path 113 is transferred into the chamber 131. Subsequently, in step S12, the controller 351 causes liquid in the liquid storage portion 210 to be transferred into the chamber.

Figure 12:
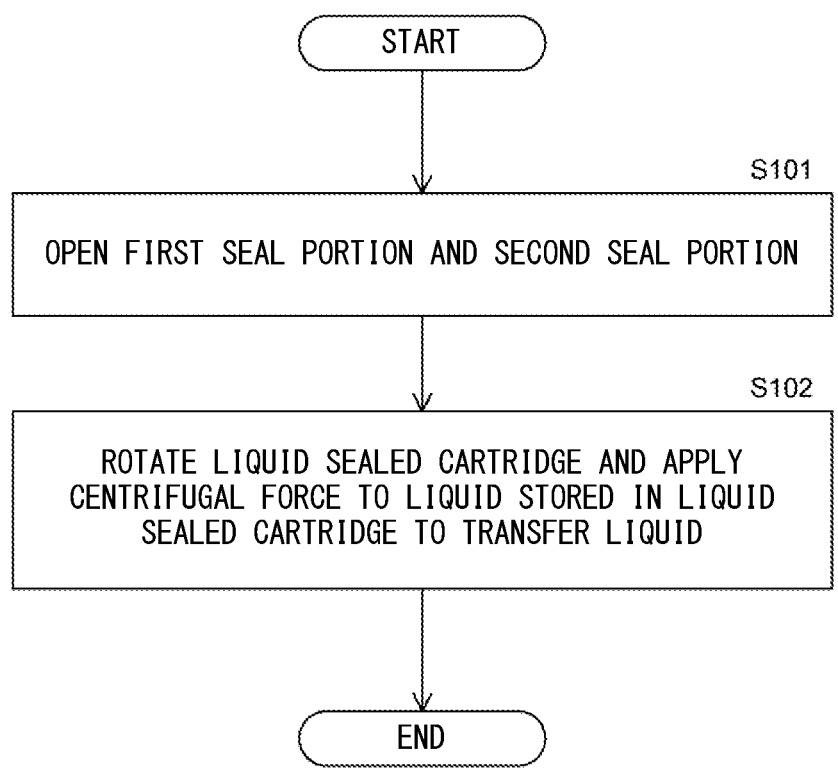
FIG. 12 is a flow chart showing a method for sending liquid according to Embodiment 1.

FIG. 12 is a flow chart showing in detail step S12 shown in FIG. 11.

In step S101, the controller 351 causes the first seal portion 211 and the second seal portion 212 to be opened. Specifically, the controller 351 drives the motor 317 to rotate the liquid sealed cartridge 100 such that the first seal portion 211 and the second seal portion 212 aligned in the radial direction are disposed vertically below the two pressing portions 324. The controller 351 drives the two pressing portions 324 to press down and open the first seal portion 211 and the second seal portion 212. The controller 351 causes such an opening operation to be repeatedly performed, and the first seal portion 211 and the second seal portion 212 of each of the liquid supply sections 121 to 127 are opened. By the first seal portion 211 being opened, the liquid storage portion 210 and the transfer flow path 243 are connected to each other. By the second seal portion 212 being opened, the liquid storage portion 210 and the air flow path through which air is introduced into the liquid storage portion 210 are connected to each other.

In step S102, the controller 351 drives the motor 317 to rotate the liquid sealed cartridge 100 such that a centrifugal force is applied to the liquid stored in the liquid sealed cartridge 100, to transfer the liquid. Thus, as described with reference to FIG. 5A to FIG. 5C, the liquid in the liquid storage portion 210 and the bypass flow path 220 is transferred into the transfer flow path 243 without leaving the liquid therein, and transferred into a corresponding chamber.

In step S102, the R1 reagent in the liquid storage portion 210 and the bypass flow path 220 of the liquid supply section 121 is transferred into the chamber 131. The R2 reagent in the liquid storage portion 210 and the bypass flow path 220 of the liquid supply section 122 is transferred into the chamber 131. In the chamber 131, the plasma component, the R1 reagent, and the R2 reagent are mixed. The R3 reagent in the liquid storage portion 210 and the bypass flow path 220 of the liquid supply section 123 is transferred into the chamber 132. Washing liquid in the liquid storage portions 210 and the bypass flow paths 220 of the liquid supply sections 124 to 126 is transferred into the chambers 133 to 135, respectively. The R4 reagent in the liquid storage portion 210 and the bypass flow path 220 of the liquid supply section 127 is transferred into the chamber 136.

Returning to FIG. 11, when the transfer of the liquid has been ended in step S12, the controller 351 causes agitation to be performed. Specifically, the controller 351 drives the motor 317 such that, while the motor 317 rotates in a predetermined direction, switching between two different rotation speeds is performed at predetermined time intervals. Thus, Euler force generated in the rotating direction changes at predetermined time intervals, whereby the liquid in each of the chambers 131 to 136 is agitated. Such agitation is similarly performed not only in step S12 but also in steps S13 to S18 after the transfer process.

The R1 reagent includes a capture substance that binds to the test substance. The capture substance includes, for example, an antibody that binds to the test substance. The antibody is, for example, a biotin-bound HBs monoclonal antibody. The R2 reagent includes magnetic particles and magnetic particle suspension. The magnetic particles are, for example, streptavidin-bound magnetic particles the surfaces of which are coated with avidin. In step S12, the plasma component separated from the blood specimen, the R1 reagent, and the R2 reagent are mixed and agitated, whereby the test substance and the R1 reagent bind to each other by antigen-antibody reaction. By reaction between antigen-antibody reaction product and the magnetic particles, the test substance bound to the capture substance in the R1 reagent binds to the magnetic particles by means of the capture substance. Thus, a complex in which the test substance and the magnetic particles bind to each other, is generated.

Next, in step S13, the controller 351 causes the complex in the chamber 131 to be transferred from the chamber 131 into the chamber 132.

Specifically, the controller 351 drives the motor 317 to rotate the liquid sealed cartridge 100 such that the chamber 131 is positioned vertically above the magnet of the magnetic force application section 314. The controller 351 drives the magnetic force application section 314 to move the magnet close to the lower surface of the liquid sealed cartridge 100 such that the complex that spreads in the chamber 131 is collected. The controller 351 drives the magnetic force application section 314 to move the magnet inward in the radial direction such that the complex in the chamber 131 is transferred into the flow path 115 that is arc-shaped. The controller 351 drives the motor 317 to rotate the liquid sealed cartridge 100 such that the complex is transferred along the flow path 115. The controller 351 drives the magnetic force application section 314 to move the magnet outward in the radial direction such that the complex is transferred into the chamber 132. The controller 351 drives the magnetic force application section 314 to separate the magnet from the lower surface of the liquid sealed cartridge 100.

As described above, the process step of step S13 is performed. The transfer of the complex in each of steps S14 to S17 is also performed in the same manner as in step S13.

Thus, the complex generated in the chamber 131 and the R3 reagent are mixed with each other in the chamber 132. The R3 reagent includes a labeling substance. The labeling substance includes: a capture substance that specifically binds to the test substance; and a label. For example, the labeling substance is a labelled antibody which includes an antibody used as the capture substance. In step S13, the complex generated in the chamber 131 and the R3 reagent are mixed and agitated, so that the complex and the labelled antibody contained in the R3 reagent react with each other. Thus, a complex in which the test substance, the capture antibody, the magnetic particles, and the labelled antibody are bound, is generated.

In step S14, the controller 351 causes the complex in the chamber 132 to be transferred from the chamber 132 into the chamber 133. Thus, in the chamber 133, the complex generated in the chamber 132 and the washing liquid are mixed. In step S14, by the complex generated in the chamber 132 and the washing liquid being mixed and agitated, the complex and unreacted substances are separated from each other in the chamber 133. That is, in the chamber 133, the unreacted substances are removed by washing.

In step S15, the controller 351 causes the complex in the chamber 133 to be transferred from the chamber 133 into the chamber 134. Thus, in the chamber 134, the complex generated in the chamber 132 and the washing liquid are mixed. Also in the chamber 134, unreacted substances are removed by washing.

In step S16, the controller 351 causes the complex in the chamber 134 to be transferred from the chamber 134 into the chamber 135. Thus, in the chamber 135, the complex generated in the chamber 132 and the washing liquid are mixed. Also in the chamber 135, unreacted substances are removed by washing.

In step S17, the controller 351 causes the complex in the chamber 135 to be transferred from the chamber 135 into the chamber 136. Thus, in the chamber 136, the complex generated in the chamber 132 and the R4 reagent are mixed. The R4 reagent is a reagent for dispersing the complex generated in the chamber 132. The R4 reagent is, for example, a buffer. In step S17, the complex generated in the chamber 132 and the R4 reagent are mixed and agitated, whereby the complex generated in the chamber 132 is dispersed.

In step S18, the controller 351 causes the R5 reagent to be transferred into the chamber 136. Specifically, similarly to step S12, the controller 351 causes the first seal portion 211 and the second seal portion 212 of the liquid supply section 128 to be opened, and a centrifugal force is applied to the R5 reagent in the liquid storage portion 210 and the bypass flow path 220 of the liquid supply section 128, whereby the R5 reagent is transferred into the transfer flow path 243. Thus, the R5 reagent is transferred into the chamber 136, and, in the chamber 136, the mixture generated in step S17 is further mixed with the R5 reagent.

The R5 reagent is a luminescent reagent containing a luminescent substrate that generates light by reaction with the labelled antibody bound to the complex. In step S18, the mixture generated in step S17 and the R5 reagent are mixed and agitated, to prepare a sample. The sample causes chemiluminescence by reaction between the luminescent substrate and the labeling substance bound to the complex.

In step S19, the controller 351 drives the motor 317 to rotate the liquid sealed cartridge 100 such that the chamber 136 is positioned vertically above the light detector of the detector 315, and light generated from the chamber 136 is detected by the light detector. In step S20, the controller 351 performs immune analysis on the basis of the light detected by the light detector of the detector 315. In a case where the light detector of the detector 315 is implemented as a photomultiplier, a pulse waveform based on reception of photons is outputted from the light detector. The detector 315 counts the photons at regular intervals on the basis of the output signal from the light detector, and outputs the counted value. The controller 351 performs analysis for presence or absence of the test substance and an amount of the test substance on the basis of the counted value outputted by the detector 315, and causes the display unit 352 to display the result of the analysis.

Next, Embodiments 2 to 5 in each of which a part of the structure of the liquid supply section 121 to 128 is changed will be described with reference to FIG. 13A to FIG. 14B. The liquid supply sections 121 to 128 have the same structure, and the structure of the liquid supply section 127 will be described below for convenience.

Embodiment 2

Figure 13A:
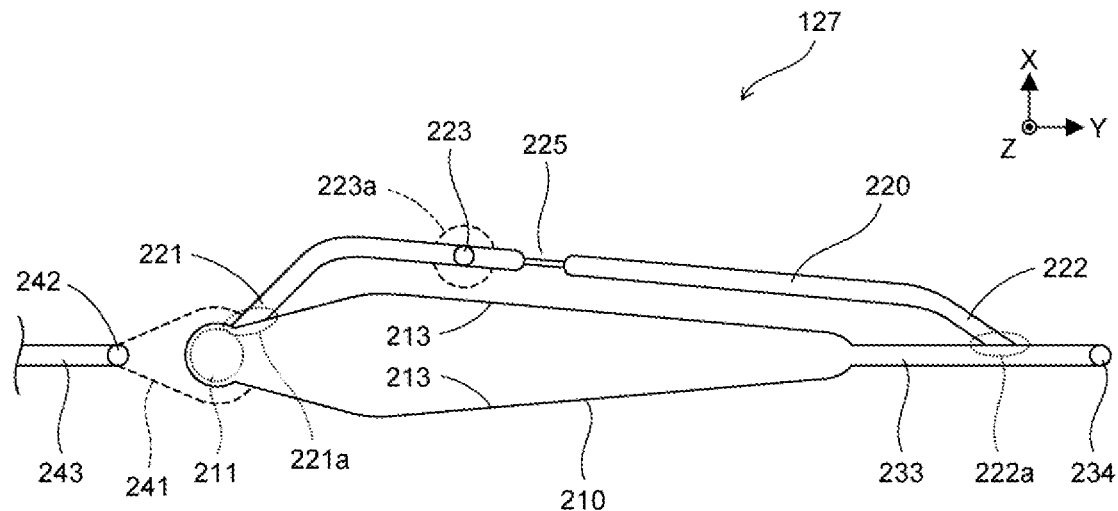
FIG. 13A is a schematic diagram illustrating a structure of a liquid supply section according to Embodiment 2.

As shown in FIG. 13A, the liquid supply section 127 of Embodiment 2 is different from that of Embodiment 1 in that, in Embodiment 2, the second seal portion 212, the air opening 224, the recess 231, and the connection flow path 232 are omitted. The end portion, of the liquid storage portion 210, on the Y-axis positive direction side is connected to the air introduction path 233, and the other end 222 of the bypass flow path 220 is connected to the air introduction path 233. The other components are the same as those of Embodiment 1.

In Embodiment 2, similarly to Embodiment 1, the liquid injected through the inlet 223 moves through the one end 221 into the liquid storage portion 210. At this time, the hole 234 is connected to the inside of the liquid storage portion 210. The hole 234 is opened before the liquid is injected, and air in the liquid storage portion 210 is discharged through the hole 234. When the injection of the liquid is ended, the inlet 223 and the hole 234 are closed with the films 104 and 105, respectively. In the measurement operation, the film 105 that has closed the hole 234 is removed. By a centrifugal force being applied to the liquid sealed cartridge 100, air is introduced through the hole 234 into the liquid storage portion 210 and the bypass flow path 220.

In Embodiment 2, the hole 234 acts as a discharge outlet of air that has been in the liquid storage portion 210 before the injection, and an introduction inlet through which air is introduced when the liquid is sent. The air introduction path 233 and the hole 234 act as an air flow path that connects between the liquid storage portion 210, and the hole 234 corresponding to the introduction inlet. Thus, in Embodiment 2, the hole 234 doubles as an air discharge outlet and an air introduction inlet, whereby the structure of the liquid sealed cartridge 100 is simplified.

Also in Embodiment 2, similarly to Embodiment 1, liquid can be smoothly injected while the liquid is prevented from leaking during injection of the liquid. When liquid is sent, air can be introduced into the liquid storage portion 210 and the bypass flow path 220. Therefore, liquid can be inhibited from being left in the liquid storage portion 210 and the bypass flow path 220.

Embodiment 3

Figure 13B:
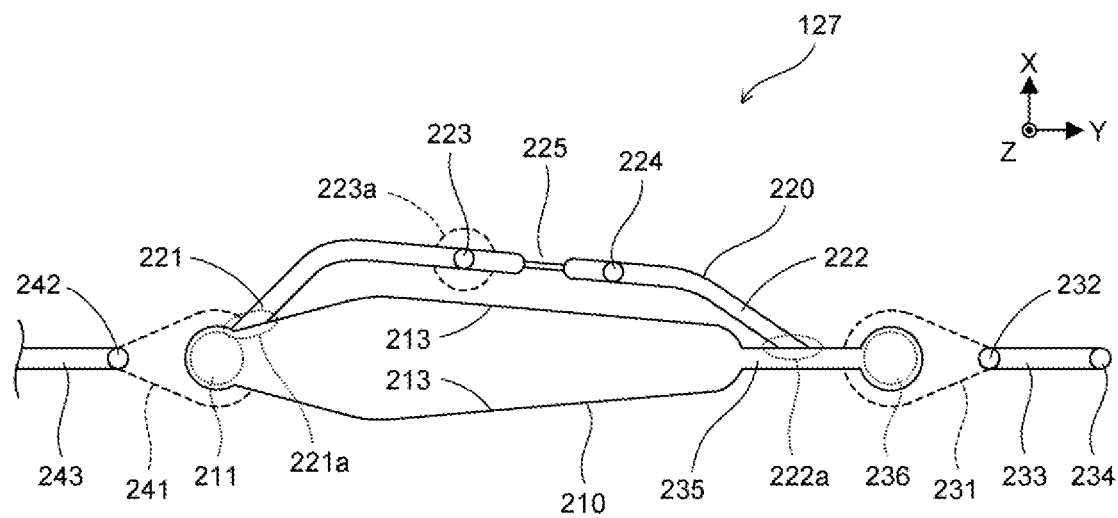
FIG. 13B is a schematic diagram illustrating a structure of a liquid supply section according to Embodiment 3.

As shown in FIG. 13B, the liquid supply section 127 of Embodiment 3 is different from that of Embodiment 1 in that, in Embodiment 3, the second seal portion 212 is eliminated from the liquid storage portion 210. A flow path 235 is connected to the Y-axis positive direction side portion of the liquid storage portion 210, and a second seal portion 236 is disposed at the Y-axis positive direction side portion of the flow path 235. The other end 222 of the bypass flow path 220 is connected to the flow path 235. The recess 231 is disposed in the Z-axis negative direction side portion of the second seal portion 236. The other components are the same as those of Embodiment 1.

Also in Embodiment 3, in a manner similar to that in Embodiment 1, liquid can be injected. When the liquid is sent, the first seal portion 211 and the second seal portion 236 are opened, whereby the liquid can be sent similarly to Embodiment 1.

Embodiment 4

Figure 14A:
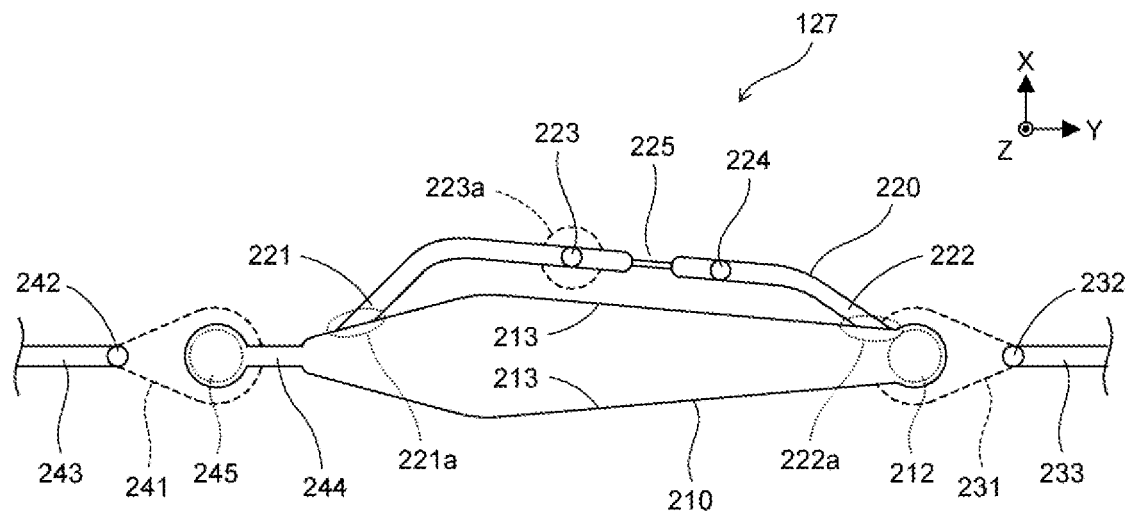
FIG. 14A is a schematic diagram illustrating a structure of a liquid supply section according to Embodiment 4.

As shown in FIG. 14A, the liquid supply section 127 of Embodiment 4 is different from that of Embodiment 1 in that, in Embodiment 4, the first seal portion 211 is eliminated from the liquid storage portion 210. A flow path 244 is connected to the Y-axis negative direction side portion of the liquid storage portion 210, and a first seal portion 245 is disposed at the Y-axis negative direction side portion of the flow path 244. The recess 241 is disposed at the Z-axis negative direction side portion of the first seal portion 245. The other components are the same as those of Embodiment 1.

Also in Embodiment 4, in a manner similar to that in Embodiment 1, liquid can be injected. When the liquid is sent, the first seal portion 245 and the second seal portion 212 are opened, whereby the liquid can be sent similarly to Embodiment 1.

Embodiment 5

Figure 14B:
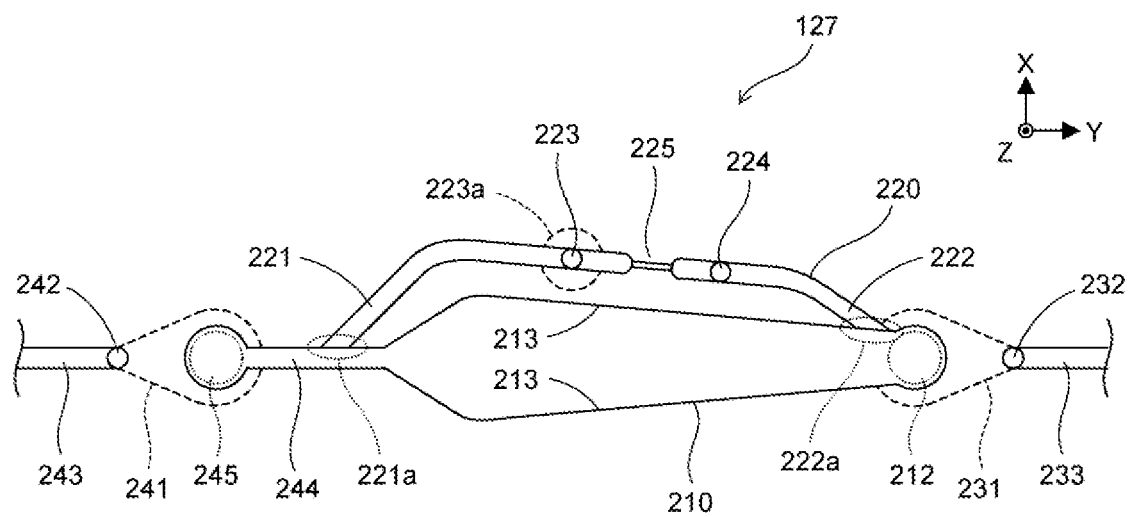
FIG. 14B is a schematic diagram illustrating a structure of a liquid supply section according to Embodiment 5.

As shown in FIG. 14B, the liquid supply section 127 of Embodiment 5 is different from that of Embodiment 4 in that, in Embodiment 5, the one end 221 of the bypass flow path 220 is connected to the flow path 244. The other components are the same as those of Embodiment 4.

In Embodiment 5, when liquid is injected, liquid that flows through the one end 221 into the flow path 244 moves through the flow path 244 into the liquid storage portion 210. Therefore, also in Embodiment 5, in a manner similar to that in Embodiment 1, liquid can be injected. When liquid is sent, the first seal portion 245 and the second seal portion 212 are opened, whereby liquid can be sent similarly to Embodiment 1.

Embodiment 6

Figure 15:
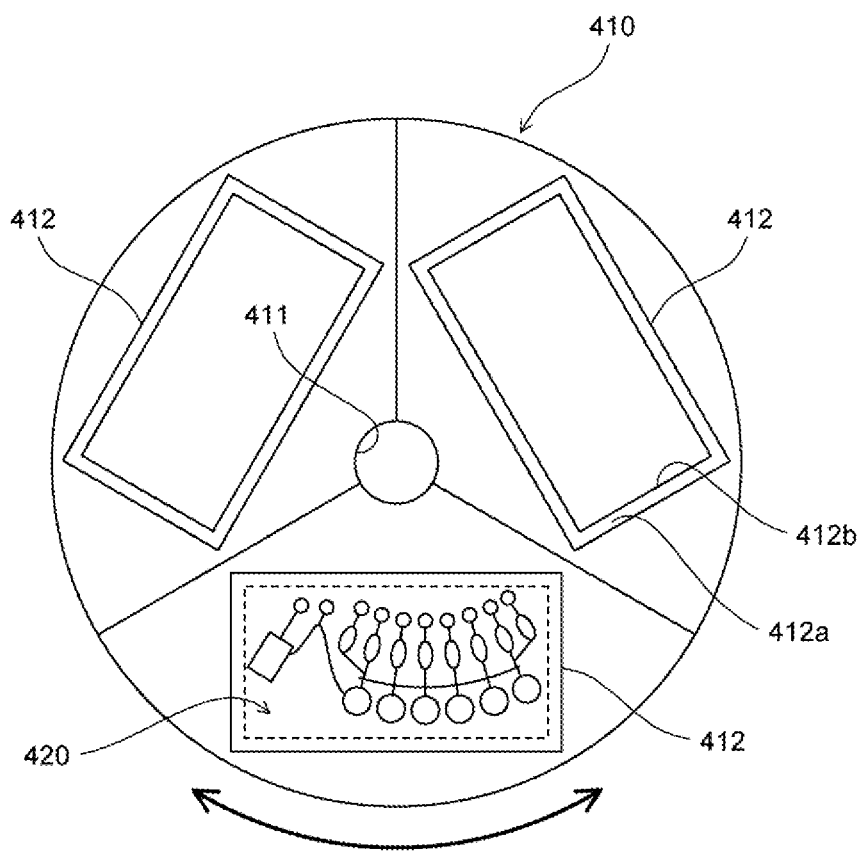
FIG. 15 is a schematic diagram illustrating structures of a support member and a liquid sealed cartridge as viewed from thereabove, according to Embodiment 6.
Figure 16:
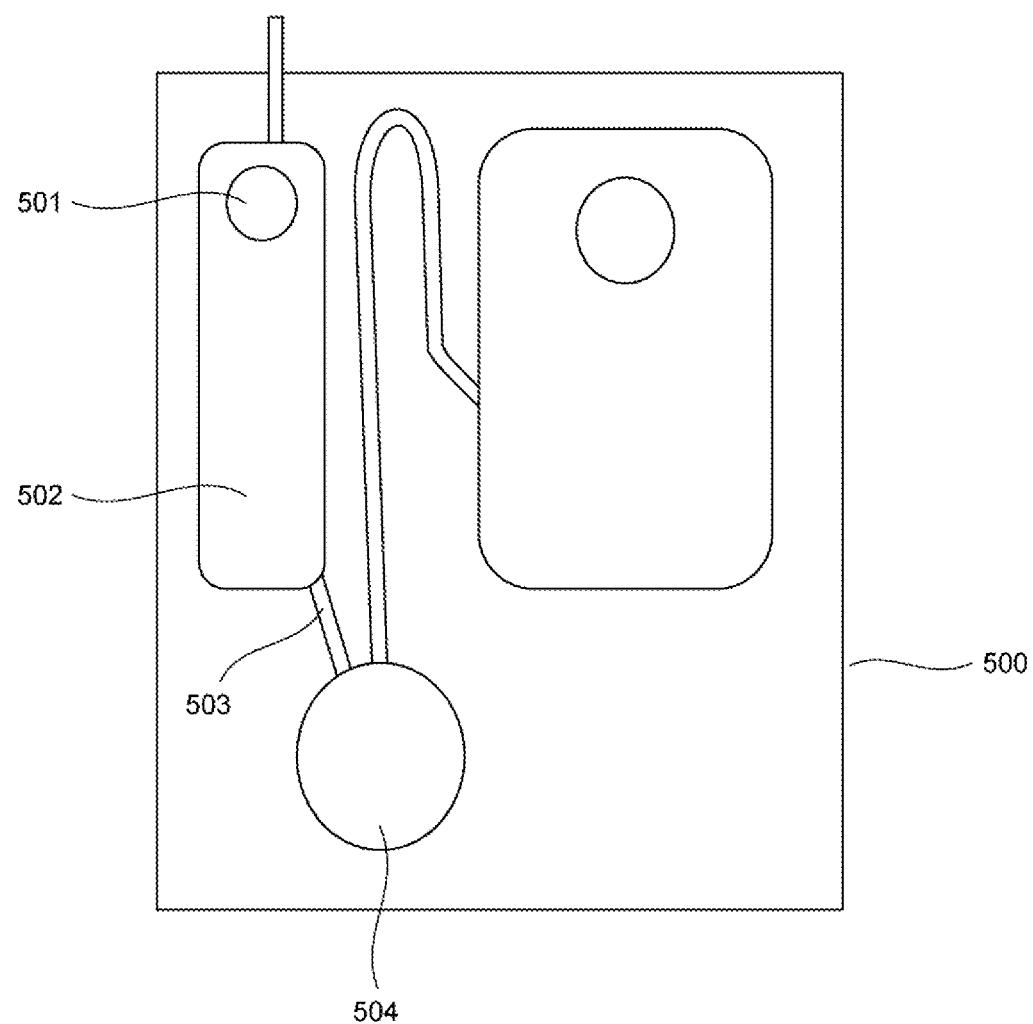
FIG. 16 is a schematic diagram illustrating a structure of a related art.

Embodiment 6 is different from Embodiment 1 in that a support member 410 is disposed instead of the support member 313 and a liquid sealed cartridge 420 is used instead of the liquid sealed cartridge 100, as shown in FIG. 15. The other components are the same as those of Embodiment 1.

The support member 410 includes a hole 411 and three placement portions 412. The hole 411 is disposed at the center of the support member 410. The support member 410 is mounted to the rotation shaft 310. Thus, the support member 410 is rotatable about the rotation shaft 310. The three placement portions 412 are provided in the rotating direction. Each placement portion 412 has a surface 412a and a hole 412b. The surface 412a is formed so as to be one level lower than the upper surface of the support member 410. The hole 412b is formed at the center of the surface 412a, and penetrates through the support member 410 in the up-down direction. The liquid sealed cartridge 420 has a rectangular shape. The liquid sealed cartridge 420 has the same structure as the liquid sealed cartridge 100 except for the outer shape.

When measurement is started, an operator injects a blood specimen through an inlet of the liquid sealed cartridge 420, and places the liquid sealed cartridge 420 on the placement portion 412, similarly to the liquid sealed cartridge 100. Similarly to Embodiment 1, the controller 351 drives the motor 317, the magnetic force application section 314, and the detector 315. In Embodiment 6, the liquid sealed cartridge 420 can be mounted to each of the three placement portions 412, whereby measurement can be simultaneously performed for the three liquid sealed cartridges 420.

What is claimed is:

1. A liquid cartridge comprising:
an engagement part formed to engage a rotation shaft;
a liquid storage configured to store liquid;
a bypass flow path having a first end and a second end connected to the liquid storage;
the bypass flow path comprising:
an inlet opening provided in the bypass flow path and configured to connect the bypass flow path to an exterior of the liquid cartridge and to receive a liquid therethrough; and
an air opening provided in the bypass flow path and configured to connect the bypass flow path to the exterior of the liquid cartridge and to discharge air in response to the liquid being injected through the inlet opening; and
a transfer flow path coupled to the liquid storage at a transfer flow path connection location that is further from the engagement part than the first end of the bypass flow path and the second end of the bypass flow path, wherein the transfer flow path is configured to transfer liquid from the liquid storage when centrifugal force is applied to the liquid cartridge.

2. The liquid cartridge of claim 1, wherein
the bypass flow path has a first cross-sectional area perpendicular to a longitudinal direction of the bypass flow path that is smaller than a first cross-sectional area of the liquid storage, wherein the first cross-sectional area of the liquid storage is perpendicular to a longitudinal direction of the liquid storage.

3. The liquid cartridge of claim 1, further comprising at least one seal portion configured to seal the liquid storage.

4. The liquid cartridge of claim 3, wherein
the at least one seal portion comprises a first seal portion provided between the liquid storage and the transfer flow path and configured to seal the liquid storage from the transfer flow path.

5. The liquid cartridge of claim 3, further comprising an air flow path through which air is introduced into the liquid storage, wherein the at least one seal portion comprises a second seal portion provided between the liquid storage and the air flow path and configured to seal the liquid storage from the air flow path.

6. The liquid cartridge of claim 1, wherein
the bypass flow path further comprises, between the air opening and the inlet opening, a liquid stopper configured to allow the air to pass therethrough and inhibit the liquid from passing therethrough.

7. The liquid cartridge of claim 6, wherein
the liquid stopper is a narrow portion having a cross-sectional area that is smaller than a first cross-sectional of the bypass flow path disposed between the inlet opening and the first end.

8. The liquid cartridge of claim 6, wherein
the liquid stopper is a hydrophobic portion that has an inner surface having a hydrophobicity higher than a hydrophobicity of an inner surface of the bypass flow path between the inlet opening and the second end.

9. The liquid cartridge of claim 1, further comprising:
a first seal film applied to the inlet opening and sealing the inlet opening from the exterior of the liquid cartridge.

10. The liquid cartridge of claim 1, further comprising:
a second seal film applied to the air opening and sealing the air opening from the exterior of the liquid cartridge.

11. The liquid cartridge of claim 1, further comprising:
a plurality of liquid storages aligned in a circumferential direction of a circle around the engagement part disposed at a center of the circle, wherein each liquid storage of the plurality of the liquid storages has a pair of inner walls that extend along two radial directions of the circle around the engagement part disposed at the center of the circle.

12. The liquid cartridge of claim 1, wherein
the first end is disposed closer to the transfer flow path than the second end.

13. The liquid cartridge of claim 1, wherein the first end and the second end of the bypass flow path are connected to the liquid storage at two radially spaced locations of the liquid storage relative to the engagement part.

14. The liquid cartridge of claim 1, wherein
the inlet opening is configured to receive the liquid therethrough from the exterior of the liquid cartridge, and
the air opening is configured to discharge the air to the exterior of the liquid cartridge.

* * * * *